(12) United States Patent
Hirschmann et al.

(10) Patent No.: US 6,902,777 B2
(45) Date of Patent: Jun. 7, 2005

(54) LIQUID-CRYSTALLINE MEDIUM

(75) Inventors: Harald Hirschmann, Darmstadt (DE); Eike Poetsch, Muehltal (DE); Peer Kirsch, Seeheim-Jugenheim (DE); Sabine Schoen, Herten (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/740,601

(22) Filed: Dec. 22, 2003

(65) Prior Publication Data
US 2004/0140452 A1 Jul. 22, 2004

(30) Foreign Application Priority Data
Dec. 21, 2002 (DE) .......................... 102 60 517

(51) Int. Cl.[7] .................. C09K 19/34; C09K 19/30; C09K 19/20; G02F 1/13; C07D 309/02; C07D 309/16

(52) U.S. Cl. ............. 428/1.1; 252/299.61; 252/299.63; 252/299.66; 252/299.67; 549/356; 549/414; 549/416; 549/417; 549/426; 549/427; 549/428; 349/186

(58) Field of Search ....................... 428/1.1; 252/299.61, 252/299.63, 299.66, 299.67; 349/186; 549/356, 416, 427, 428; 570/144

(56) References Cited

U.S. PATENT DOCUMENTS 6,329,027 B1 * 12/2001 Kondo et al. ................. 428/1.1
6,558,758 B1 * 5/2003 Yanai et al. .................. 428/1.1

\* cited by examiner

*Primary Examiner*—Shean C. Wu
(74) *Attorney, Agent, or Firm*—Millen, White, Zelano, Branigan, P.C.

(57) ABSTRACT

A liquid-crystalline mediums which contain one or more compounds of the formula A

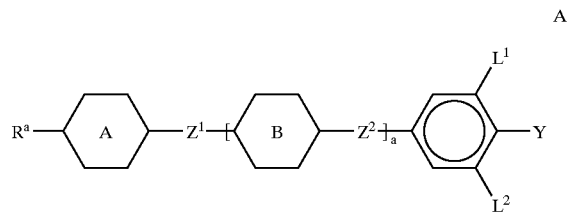

and at least one compound of the formula B

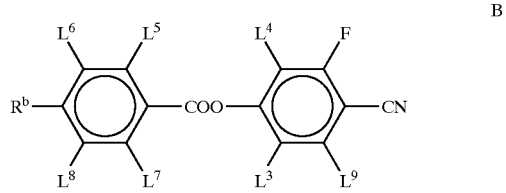

wherein compounds of formula A contain at least one ring selected from

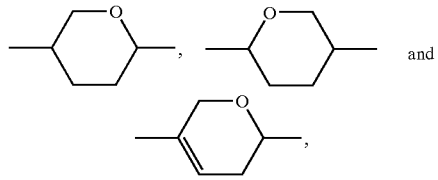

and in which $R^a$, $R^b$, ring A and ring B, Y, $Z^1$, $Z^2$, a, $L^1$, $L^2$, $L^3$, $L^4$, $L^5$, $L^6$, $L^7$, $L^8$ and $L^9$ are as defined herein, are suitable for use in twisted nematic (TN) and supertwisted nematic (STN) liquid-crystal displays. Such displays have very short response times and good steepnesses and angle dependencies.

39 Claims, No Drawings

LIQUID-CRYSTALLINE MEDIUM

The invention relates to liquid-crystalline compounds containing a pyran ring, to a liquid-crystalline medium, to twisted nematic (TN) and supertwisted nematic (STN) liquid-crystal displays having very short response times and good steepnesses and angle dependencies, and to the novel nematic liquid-crystal mixtures used therein.

TN displays are known, for example from M. Schadt and W. Helfrich, Appl. Phys. Lett., 18, 127 (1971). STN displays are known, for example from EP 0 131 216 B1; DE 34 23 993 A1; EP 0 098 070 A2; M. Schadt and F. Leenhouts, 17th Freiburg Congress on Liquid Crystals (8.–10.04.87); K. Kawasaki et al., SID 87 Digest 391 (20.6); M. Schadt and F. Leenhouts, SID 87 Digest 372 (20.1); K. Katoh et al., Japanese Journal of Applied Physics, Vol. 26, No. 11, L 1784–L 1786 (1987); F. Leenhouts et al., Appl. Phys. Lett. 50 (21), 1468 (1987); H. A. van Sprang and H. G. Koopman, J. Appl. Phys. 62 (5), 1734 (1987); T. J. Scheffer and J. Nehring, Appl. Phys. Lett. 45 (10), 1021 (1984), M. Schadt and F. Leenhouts, Appl. Phys. Lett. 50 (5), 236 (1987) and E. P. Raynes, Mol. Cryst. Liq. Cryst. Letters Vol. 4 (1), pp. 1–8 (1986). The term STN here covers any relatively highly twisted display element having a twist angle with a value of between 160° and 360°, such as, for example, the display elements according to Waters et al. (C. M. Waters et al., Proc. Soc. Inf. Disp. (New York) (1985) (3rd Intern. Display Conference, Kobe, Japan), STN-LCDs (DE-A 35 03 259), SBE-LCDs (T. J. Scheffer and J. Nehring, Appl. Phys. Lett. 45 (1984) 1021), OMI-LCDs (M. Schadt and F. Leenhouts, Appl. Phys. Lett. 50 (1987), 236, DST-LCDs (EP-A 0 246 842) or BW-STN-LCDs (K. Kawasaki et al., SID 87 Digest 391 (20.6)).

STN displays are distinguished compared with standard TN displays by significantly better steepnesses of the electro-optical characteristic line and, associated therewith, better contrast values, and by significantly lower angle dependence of the contrast.

Of particular interest are TN and STN displays having very short response times, in particular also at relatively low temperatures. In order to achieve short response times, the rotational viscosities of the liquid-crystal mixtures have hitherto been optimised using mostly monotropic additives having relatively high vapour pressure. However, the response times achieved were not adequate for every application.

In order to achieve a steep electro-optical characteristic line in the displays according to the invention, the liquid-crystal mixtures should have relatively large values for the ratio between the elastic constants $K_{33}/K_{11}$ and relatively small values for $\Delta\epsilon/\epsilon_\perp$, where $\Delta\epsilon$ is the dielectric anisotropy and $\epsilon_\perp$ is the dielectric constant perpendicular to the longitudinal molecular axis.

In addition to optimisation of the contrast and response times, further important requirements are made of mixtures of this type:
1. broad d/p window
2. high long-term chemical stability
3. high electrical resistance
4. low frequency and temperature dependence of the threshold voltage.

The parameter combinations achieved are still far from adequate, in particular for high-multiplex STN displays (with a multiplex rate in the region of about 1/400), but also for medium- and low-multiplex STN displays (with multiplex rates in the region of about 1/64 and 1/16 respectively), and TN displays. This is partly attributable to the fact that the various requirements are affected in opposite manners by material parameters.

Thus, there continues to be a great demand for TN and STN displays, in particular for medium- and low-multiplex STN displays, having very short response times at the same time as a large working-temperature range, high characteristic-line steepness, good angle dependence of the contrast and low threshold voltage which meet the above-mentioned requirements.

The invention has the object of providing liquid-crystalline media, in particular for TN and STN displays, which do not have the above-mentioned disadvantages or only do so to a lesser extent and at the same time have short response times, in particular at low temperatures, and very good steepnesses. The media according to the invention are furthermore suitable for IPS (in-plane switching) applications.

It has now been found that this object can be achieved if use is made of liquid-crystal mixtures which comprise one or more compounds of the formula A

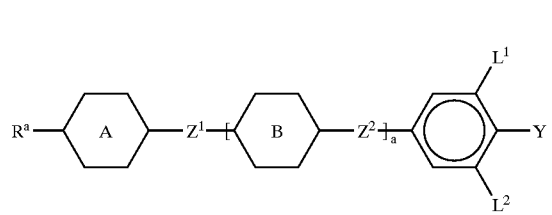

A and at least one compound of the formula B

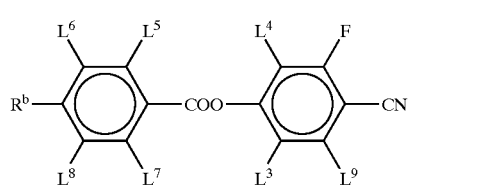

B in which $R^a$ and $R^b$ are each, independently of one another, H or an alkyl radical having from 1 to 12 carbon atoms which is unsubstituted, monosubstituted by CN or $CF_3$ or at least monosubstituted by halogen, where one or more $CH_2$ groups in these radicals may also each, independently of one another, be replaced by —O—, —S—,

—CH=CH—, —C≡C—, —CO—, —CO—O—, —O—CO— or —O—CO—O— in such a way that O atoms are not linked directly to one another,

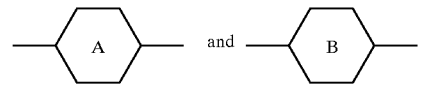

are each, independently of one another,

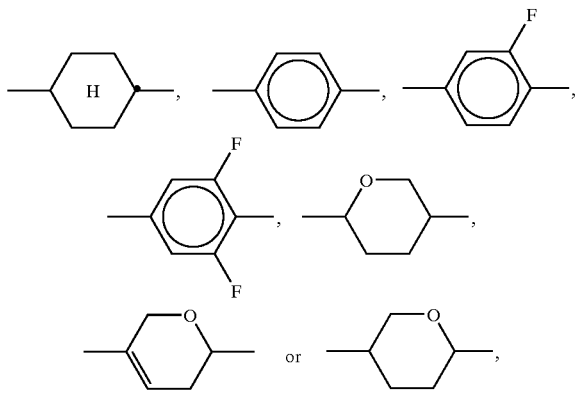

at least one ring is

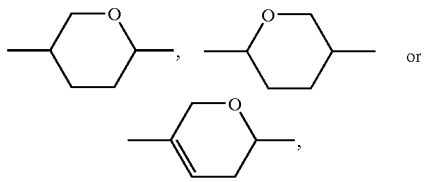

$Z^1$ and $Z^2$ are each, independently of one another, —CH$_2$CH$_2$—, —(CH$_2$)$_4$—, —CH$_2$O—, —OCH$_2$—, —CF$_2$O—, —OCF$_2$—, —C≡C—, —CF=CF—, —CH=CH—, —COO—, —CH$_2$—, —(CH$_2$)$_3$— or a single bond, a is 0 or 1, $L^1$ to $L^9$ are each, independently of one another, H or F, and Y is F, Cl, SF$_5$, NCS, SCN, CN, OCN, or a monohalogenated or polyhalogenated alkyl, alkoxy, alkenyl or alkenyloxy radical, each having up to 5 carbon atoms.

The use of compounds of the formula A containing a pyran ring in combination with compounds of the formula B gives, in particular, TN and STN mixtures which are distinguished over the prior art by relatively high clearing points, good values for the optical anisotropy (Δn) and very high values for the dielectric anisotropy and by significantly improved rotational viscosity.

The use of the compounds of the formulae A and B in the mixtures for TN and STN displays according to the invention results in high steepness of the electro-optical characteristic line, low temperature dependence of the threshold voltage, very fast response times, in particular at low temperatures.

The compounds of the formulae A and B significantly shorten, in particular, the response times of TN and STN mixtures while simultaneously increasing the steepness and reducing the temperature dependence of the threshold voltage.

The mixtures according to the invention are furthermore distinguished by the following advantages:

they have low viscosity, they have a low threshold voltage and operating voltage, and they effect long shelf lives in the display at low temperatures.

The invention furthermore relates to a liquid-crystal display having two outer plates, which, together with a frame, form a cell, a nematic liquid-crystal mixture of positive dielectric anisotropy located in the cell, electrode layers with alignment layers on the insides of the outer plates, a tilt angle between the longitudinal axis of the molecules at the surface of the outer plates and the outer plates of from 0 degree to 30 degrees, and a twist angle of the liquid-crystal mixture in the cell from alignment layer to alignment layer with a value of between 22.5° and 600°, a nematic liquid-crystal mixture consisting of a) 15–75% by weight of a liquid-crystalline component A consisting of one or more compounds having a dielectric anisotropy of greater than +1.5;

b) 2–85% by weight of a liquid-crystalline component B consisting of one or more compounds having a dielectric anisotropy of between −1.5 and +1.5;

c) 0–20% by weight of a liquid-crystalline component D consisting of one or more compounds having a dielectric anisotropy of below −1.5, and d) if desired, an optically active component C in such an amount that the ratio between the layer thickness (separation of the outer plates) and the natural pitch of the chiral nematic liquid-crystal mixture is from about 0.2 to 1.3, characterised in that component A comprises at least one compound of the formula A

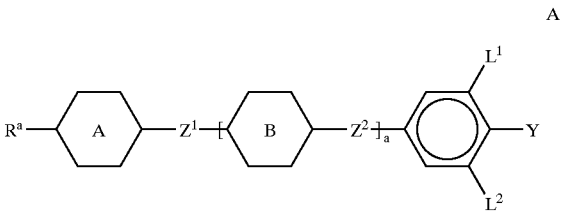

and at least one compound of the formula B

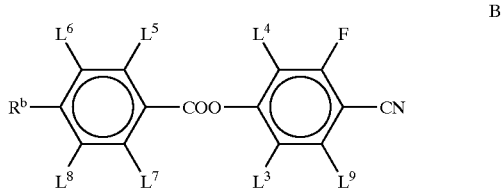

in which $R^a$, $R^b$, ring A, ring B, a, $Z^1$, $Z^2$, $L^1$, $L^2$, $L^3$, $L^4$, $L^5$, $L^6$, $L^7$, $L^8$, $L^9$ and Y are as defined above.

The invention also relates to TN and STN displays, in particular medium- and low-multiplexed STN displays, containing the liquid-crystal mixture according to the invention.

The use of the compounds of the formulae A and B in IPS mixtures results in improved response times owing to the reduced rotational viscosity and in a reduction in the driving voltage for monitor and TV applications.

Formula A covers, in particular, compounds of the sub-formulae A-1 to A-56

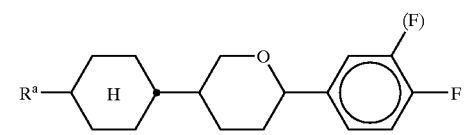 A-1
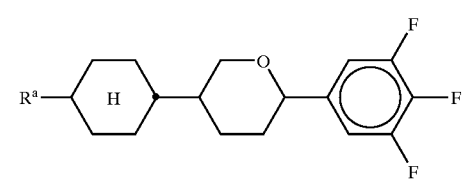 A-2
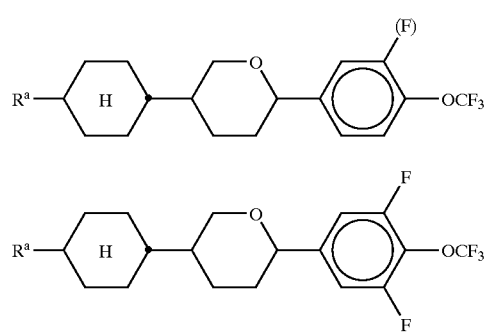 A-3
A-4
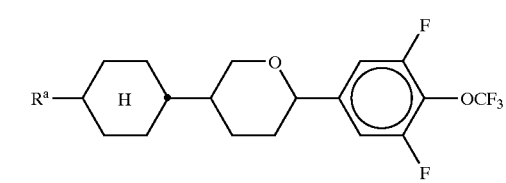 A-5
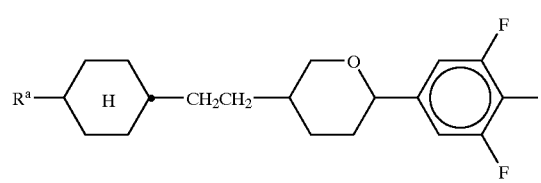 A-6
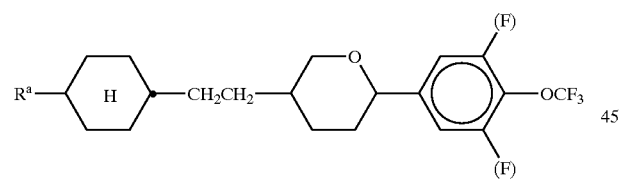 A-7
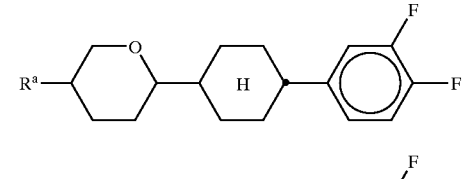 A-8
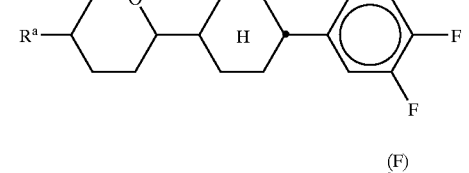 A-9
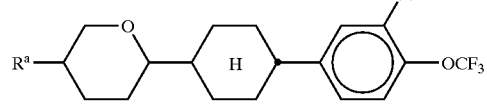
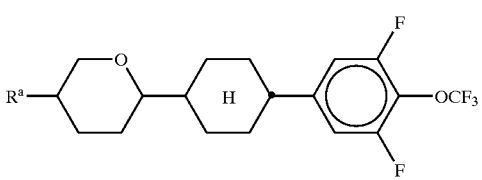
A-10
A-11
A-12
A-13
A-14
A-15
A-16
A-17
A-18
A-19

A-20
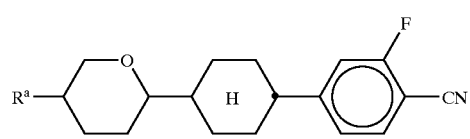
A-21
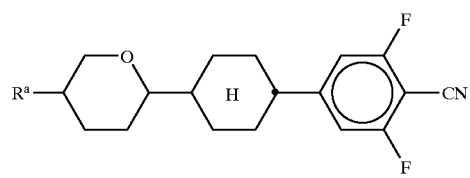
A-22
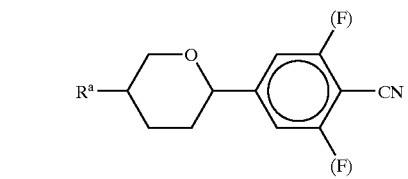
A-23
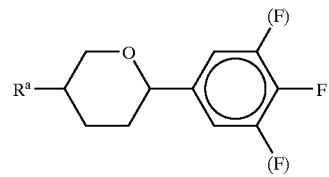
A-24
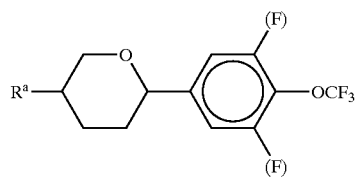
A-25
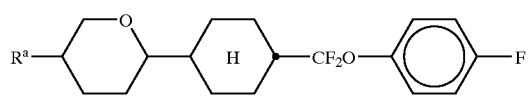
A-26
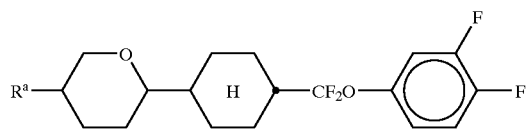
A-27
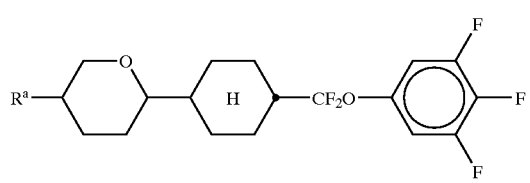
A-28
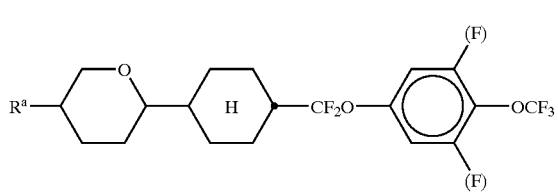
A-29
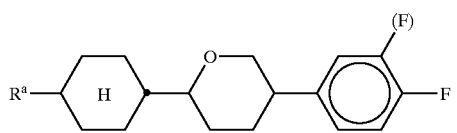
A-30
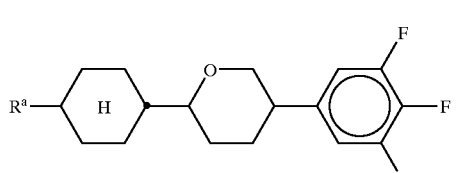
A-31
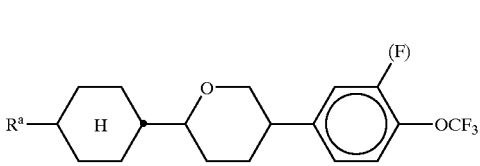
A-32
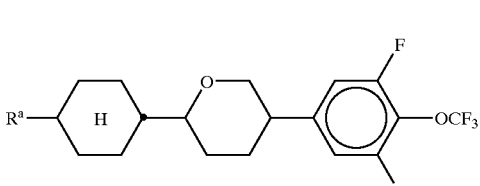
A-33
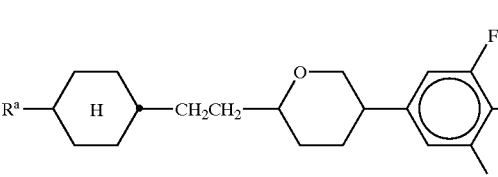
A-34
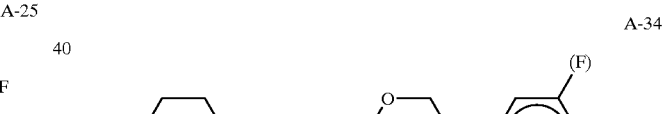
A-35
A-36
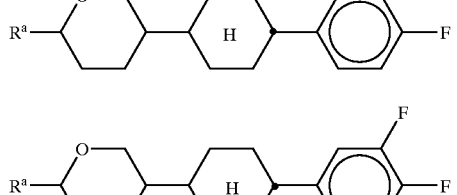
A-37
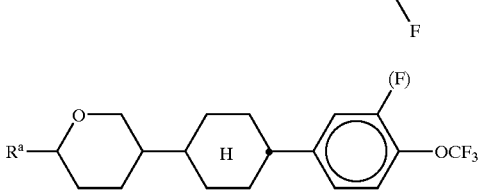

A-38 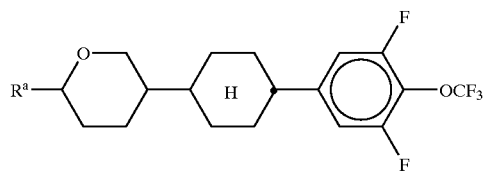
A-39 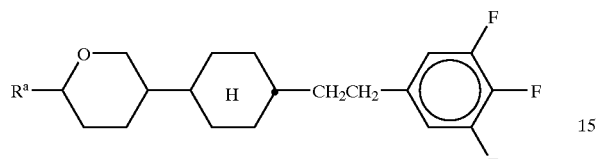
A-40 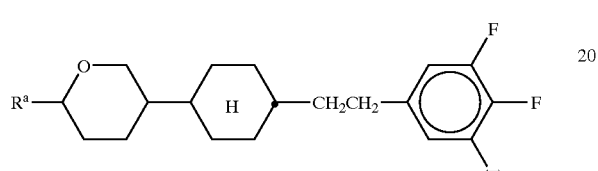
A-41 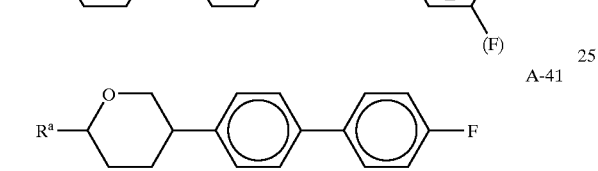
A-42 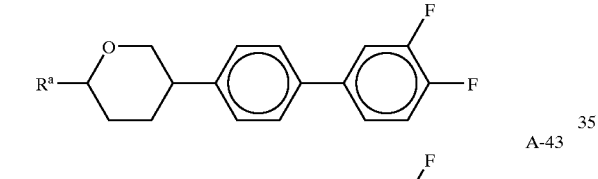
A-43 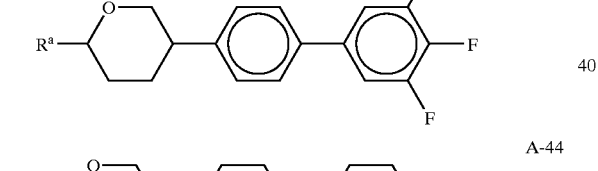
A-44 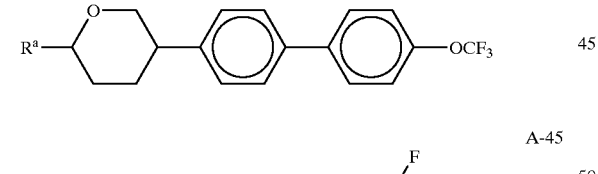
A-45 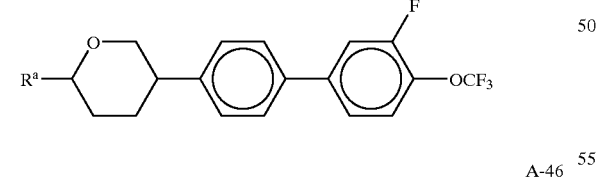
A-46 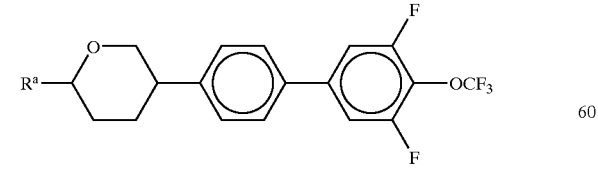
A-47 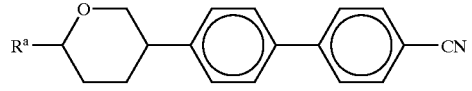
A-48 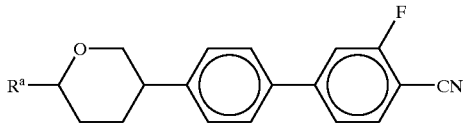
A-49 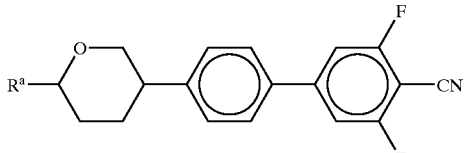
A-50 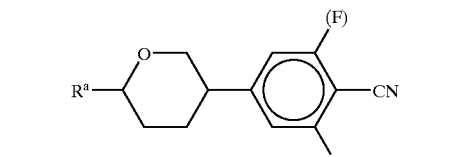
A-51 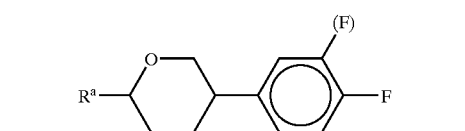
A-52 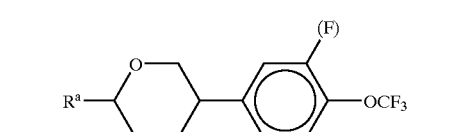
A-53 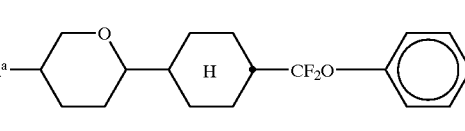
A-54 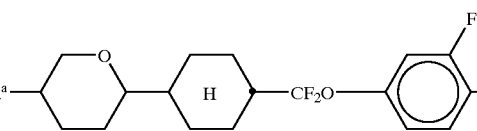
A-55 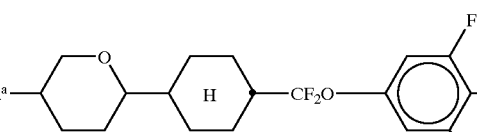
A-56 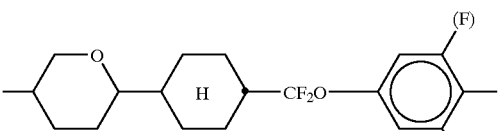
in which $R^a$ is as defined above, and (F) represents an optional F substituent.

The invention also relates to compounds of the formula A, in particular of the formulae A-1 to A-24 and A-29 to A-52.

Of the compounds of the formulae A-1 to A-56, particular preference is given in the mixtures according to the invention to the compounds of the formulae A-1, A-2, A-3, A-4, A-7, A-8, A-9, A-10, A-13, A-14, A-15, A-16, A-17, A-18, A-22, A-25, A-26, A-27 and A-28, furthermore A-29, A-30, A-31, A-32, A-35, A-36, A-37, A-38, A41, A-42, A43, A-44, A-45, A-46, A-50, A-53, A-54, A-55 and A-56.

Particular preference is given to the compounds of the formulae A-2, A-8, A-15, A-17, A-18 and A-27.

Particular preference is given to mixtures according to the invention which comprise at least one compound of the formula A-2 and/or A-8.

In the formulae A and A-1 to A-12, $R^a$ is particularly preferably straight-chain alkyl or alkoxy, 1 E-alkenyl or 3E-alkenyl having from 2 to 7 carbon atoms.

Y is preferably F, Cl, CN, $CF_3$, $C_2F_5$, $C_3F_7$, $CF_2H$, $OCF_3$, $OCF_2H$, $OCFHCF_3$, $OCFHCFH_2$, $OCFHCF_2H$, $OCF_2CH_3$, $OCF_2CFH_2$, $OCF_2CF_2H$, $OCF_2CF_2CF_2H$, $OCF_2CF_2CFH_2$, $OCFHCF_2CF_3$, $OCFHCF_2CF_2H$, $OCFHCFHCF_3$, $OCH_2CF_2CF_3$, $OCF_2CF_2CF_3$, $OCF_2CFHCFH_2$, $OCF_2CH_2CF_2H$, $OCFHCF_2CFH_2$, $OCFHCFHCF_2H$, $OCFHCH_2CF_3$, $OCH_2CFHCF_3$, $OCH_2CF_2CF_2H$, $OCF_2CFHCH_3$, $OCF_2CH_2CFH_2$, $OCFHCF_2CH_3$, $OCFHCFHCFH_2$, $OCFHCH_2CF_3$, $OCH_2CF_2CFH_2$, $OCH_2CFHCF_2H$, $OCF_2CH_2CH_3$, $OCFHCFHCH_3$, $OCFHCH_2CFH_2$, $OCH_2CF_2CH_3$, $OCH_2CFHCFH_2$, $OCH_2CH_2CF_2H$, $OCHCH_2CH_3$, $OCH_2CFHCH_3$, $OCH_2CH_2CF_2H$, $OCClFCF_3$, $OCClFCClF_2$, $OCClFCFH_2$, $OCFHCCl_2F$, $OCClFCF_2H$, $OCClFCClF_2$, $OCF_2CClH_2$, $OCF_2CCl_2H$, $OCF_2CCl_2F$, $OCF_2CClFH$, $OCF_2CClF_2$, $OCF_2CF_2CClF_2$, $OCF_2CF_2CCl_2F$, $OCClFCF_2CF_3$, $OCClFCF_2CF_2H$, $OCClFCF_2CClF_2$, $OCClFCFHCF_3$, $OCClFCClFCF_3$, $OCCl_2CF_2CF_3$, $OCClHCF_2CF_3$, $OCClFCF_2CF_3$, $OCClFCClFCF_3$, $OCF_2CClFCFH_2$, $OCF_2CF_2CCl_2F$, $OCF_2CCl_2CF_2H$, $OCF_2CH_2CClF_2$, $OCClFCF_2CFH_2$, $OCFHCF_2CCl_2F$, $OCClFCFHCF_2H$, $OCClFCClFCF_2H$, $OCFHCFHCClF_2$, $OCClFCH_2CF_3$, $OCFHCCl_2CF_3$, $OCCl_2CFHCF_3$, $OCH_2CClFCF_3$, $OCCl_2CF_2CF_2H$, $OCH_2CF_2CClF_2$, $OCF_2CClFCH_3$, $OCF_2CFHCCl_2H$, $OCF_2CCl_2CFH_2$, $OCF_2CH_2CCl_2F$, $OCClFCF_2CH_3$, $OCFHCF_2CCl_2H$, $OCClFCClFCFH_2$, $OCFHCFHCCl_2F$, $OCClFCH_2CF_3$, $OCFHCCl_2CF_3$, $OCCl_2CF_2CFH_2$, $OCH_2CF_2CCl_2F$, $OCCl_2CFHCF_2H$, $OCClHCClFCF_2H$, $OCF_2CClHCClH_2$, $OCF_2CH_2CCl_2H$, $OCClFCFHCH_3$, $OCF_2CClFCCl_2H$, $OCClFCH_2CFH_2$, $OCFHCCl_2CFH_2$, $OCCl_2CF_2CH_3$, $OCH_2CF_2CClH_2$, $OCCl_2CFHCFH_2$, $OCH_2CClFCFCl_2$, $OCH_2CH_2CF_2H$, $OCClHCClHCF_2H$, $OCH_2CCl_2CF_2H$, $OCClFCH_2CH_3$, $OCFHCH_2CCl_2H$, $OCClHCFHCClH_2$, $OCH_2CFHCCl_2H$, $OCCl_2CH_2CF_2H$, $OCH_2CCl_2CF_2H$, $CH=CF_2$, $CF=CF_2$, $OCH=CF_2$, $OCF=CF_2$, $CH=CHF$, $OCH=CHF$, $CF=CHF$, $OCF=CHF$, in particular F, Cl, CN, $CF_3$, $CF_2H$, $C_2F_5$, $C_3F_7$, $OCF_3$, $OCF_2H$, $OCFHCF_3$, $OCFHCFH_2$, $OCFHCF_2H$, $OCF_2CH_3$, $OCF_2CFH_2$, $OCF_2CF_2H$, $OCF_2CF_2CF_2H$, $OCF_2CF_2CFH_2$, $OCFHCF_2CF_3$, $OCFHCF_2CF_2H$, $OCF_2CF_2CF_3$, $OCF_2CHFCF_3$, $OCClFCF_2CF_3$.

Formula B covers, in particular, compounds of the subformulae B-1 to B-6,

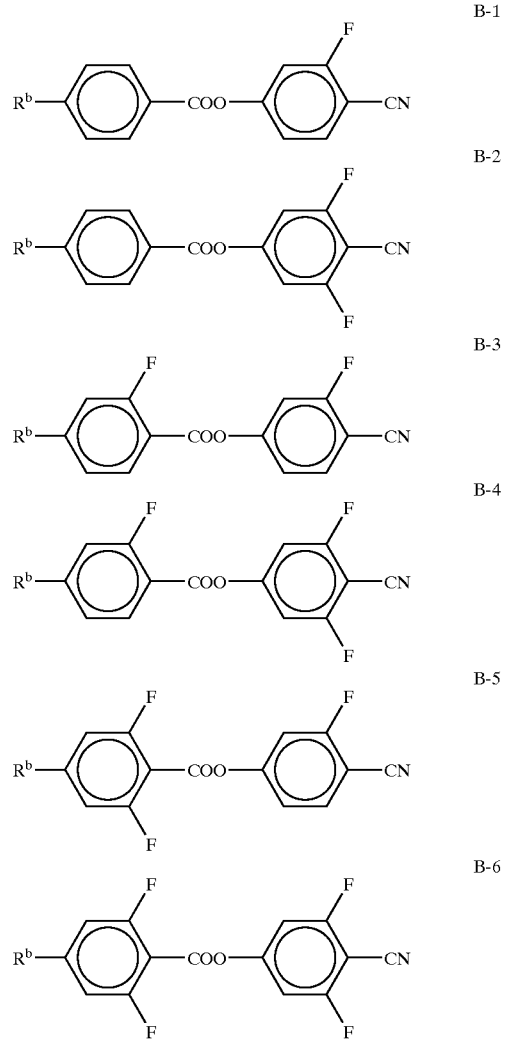

in which $R^b$ is as defined above.

Particular preference is given to compounds in which $R^b$ is a straight-chain alkyl radical having 1–7 carbon atoms or an alkenyl radical having 2–7 carbon atoms. Particular preference is given to compounds of the formulae B-1, B-2 and B4.

The use of compounds of the formulae A and B in the liquid-crystal mixtures according to the invention results in particularly low rotational viscosity values and in TN and STN displays having high steepness and fast response times, in particular at low temperatures.

Besides the compounds of the formula A, component A, or the liquid-crystalline mixture according to the invention, preferably additionally comprises one or more 3,4,5-trifluorophenyl compounds selected from the group consisting of the compounds of the formulae IIa to IIk

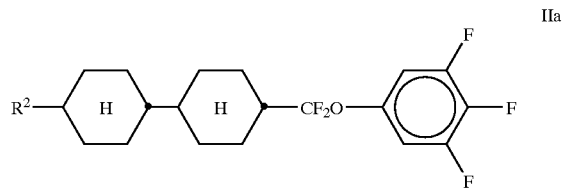

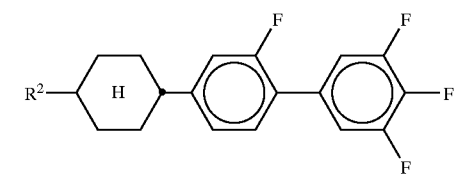 IIb

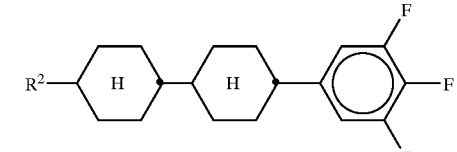 IIc

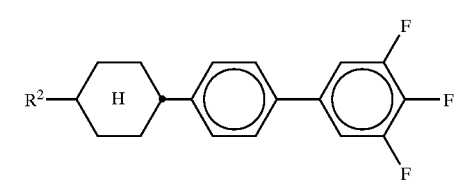 IId

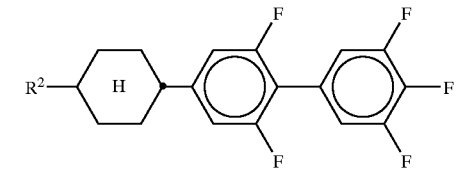 IIe

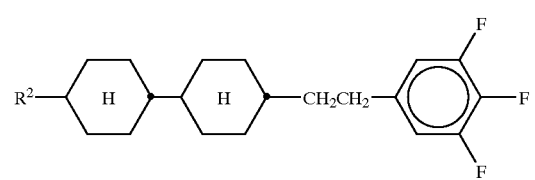 IIf

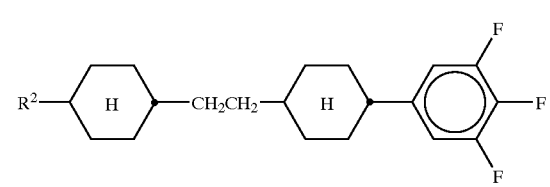 IIg

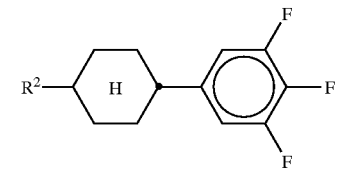 IIh

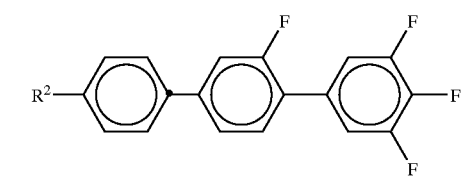 IIi

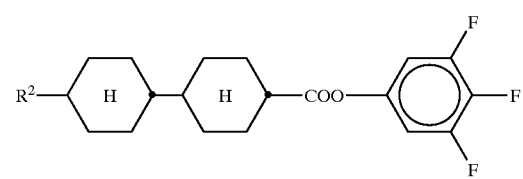 IIj

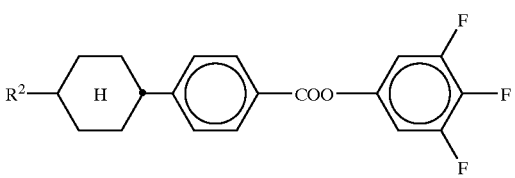 IIk in which

R² is H, an alkyl radical having from 1 to 12 carbon atoms which is unsubstituted, monosubstituted by CN or CF₃ or at least monosubstituted by halogen, where one or more CH₂ groups in these radicals may also each, independently of one another, be replaced by —O—, —S—,

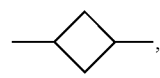

—CH=CH—, —C≡C—, —CO—, —CO—O—, —O—CO— or —O—CO—O— in such a way that O atoms are not linked directly to one another.

Besides the compounds of the formulae A and B, the medium according to the invention may additionally comprise one or more compounds containing polar end groups, of the formulae II*a to II*s

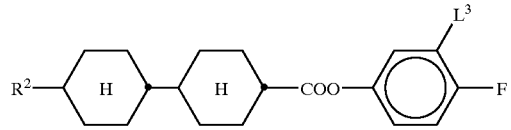 II*a

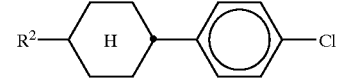 II*b

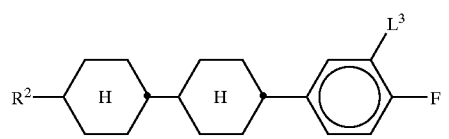 II*c

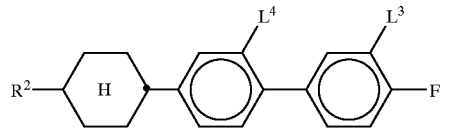 II*d

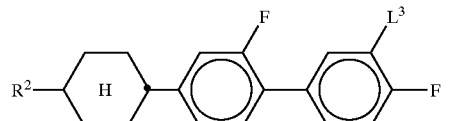 II*e

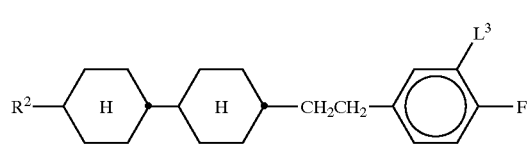 II*f

II*g
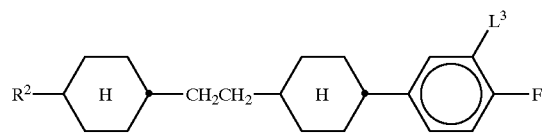

II*h
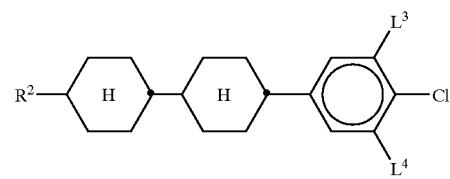

II*i
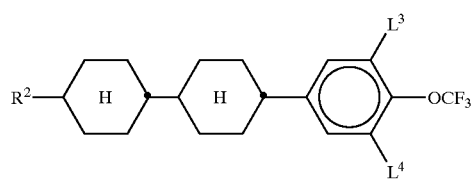

II*k
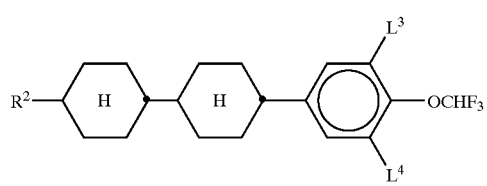

II*m
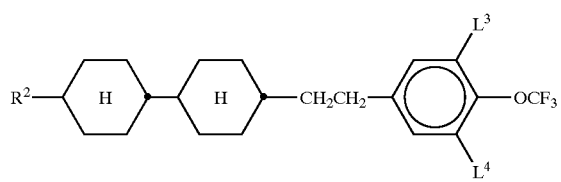

II*n
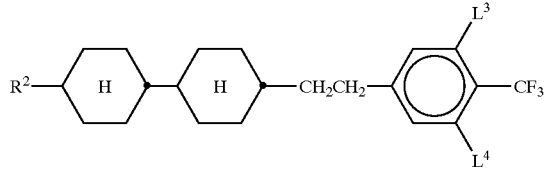

II*o
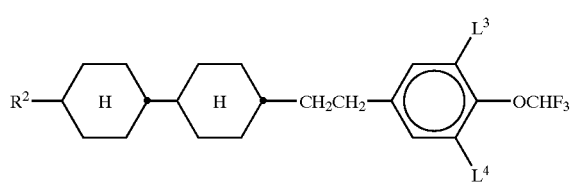

II*p
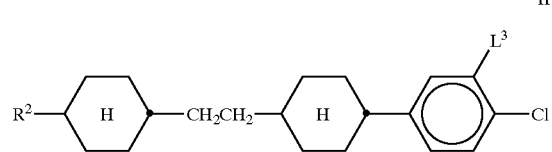

II*q
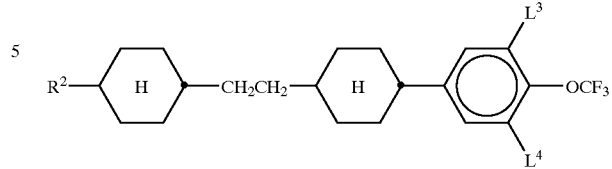

II*r
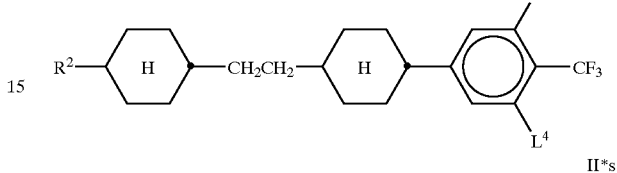

II*s
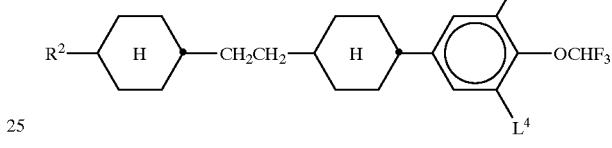

in which $R^2$ is as defined for $R^a$, and $L^3$ and $L^4$ are each, independently of one another, H or F. $R^2$ in these compounds is particularly preferably alkyl, alkenyl or alkoxy having up to 7 carbon atoms.

The medium according to the invention or component A particularly preferably comprises compounds of the formulae IIa, IIb, IIc, IId, IIe, IIf, IIg, IIj, II*b, II*c, II*d, II*f and/or II*i, in particular compounds of the formulae IIa, IIb, IId, IIi, II*a and II*i.

Besides one or more compounds of the formula B, the mixture according to the invention preferably comprises one or more cyano compounds of the formulae IIIa to IIIj:

IIIa
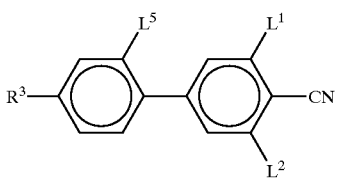

IIIb
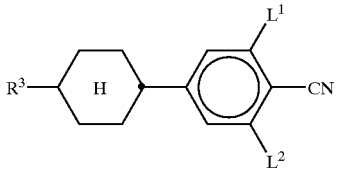

IIIc
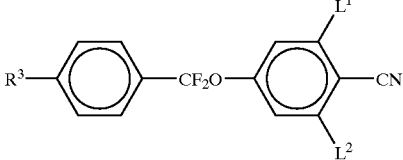

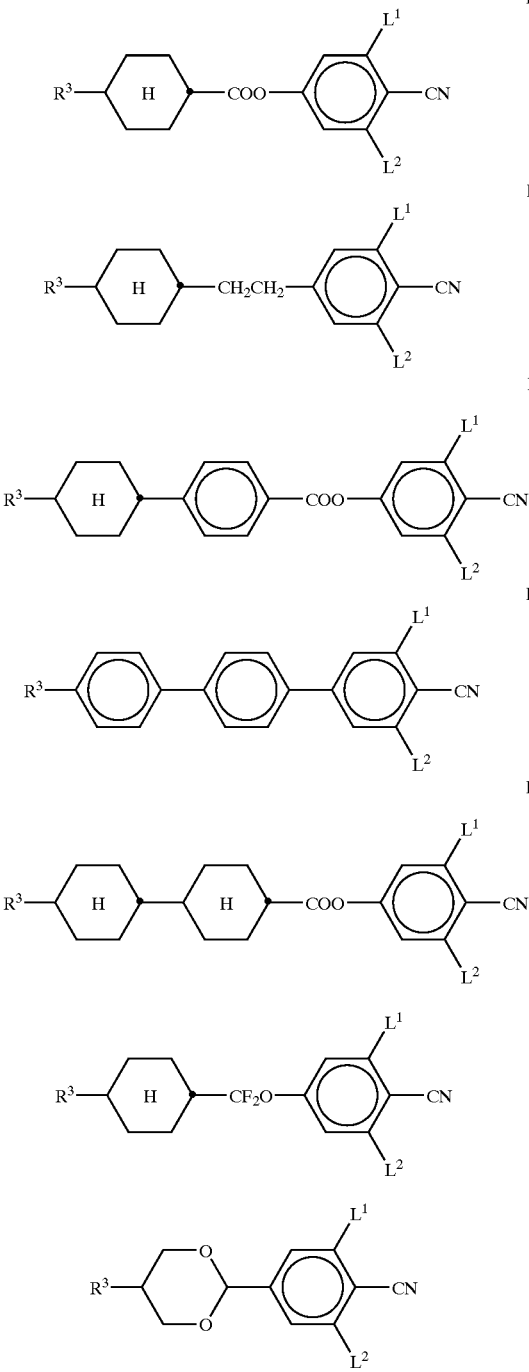

in which $R^3$ is as defined for $R^a$, and $L^1$, $L^2$ and $L^5$ are each, independently of one another, H or F. $R^3$ in these compounds is particularly preferably alkyl, alkenyl or alkoxy having up to 7 carbon atoms.

Particular preference is given to mixtures which comprise one or more compounds of the formulae IIIb, IIIc, IIIf and IIIj, in particular those in which $L^1$ and/or $L^2$ is F.

Preference is furthermore given to mixtures which comprise one or more compounds of the formula IIIf and/or IIIg in which $L^2$ is H and $L^1$ is H or F, in particular F.

The individual compounds of the formulae A, B and of the formulae IIa–IIk, II*a–II*s and IIIa to IIIj and their sub-formulae or also other compounds which can be used in the mixtures or TN and STN displays according to the invention are either known or can be prepared analogously to the known compounds.

The compounds of the formula A have low viscosities, in particular low rotational viscosities, and low values for the ratio of the elastic constants $K_{33}/K_{11}$, and therefore result in short response times in the displays according to the invention, while the presence of compounds of the formula B of high dielectric anisotropy, in particular in increased concentrations, causes a reduction in the viscosity.

Preferred liquid-crystal mixtures comprise component A in a proportion of from 15% to 75%, particularly preferably from 20% to 65%. The compounds of component A preferably have a dielectric anisotropy of $\Delta\epsilon \geq +3$, in particular of $\Delta\epsilon \geq +8$, particularly preferably of $\Delta\epsilon \geq +12$.

Further preferred mixtures comprise one or more, in particular from two to four, compounds of the formula A, in each case one, two or three compounds of the formula A, one or more, in particular one or two, compounds of the formula B, one or more, in particular from two to five, compounds of the formulae IIIa, IIIb, IIIc and/or IIIf.

Preferred liquid-crystal mixtures comprise component B in a proportion of from 2 to 85%, particularly preferably 5 to 80%, especially 5 to 75%. The compounds from group B are distinguished, in particular, by their low values for the rotational viscosity $\gamma_1$.

Component B preferably comprises one or more compounds of the formula IV

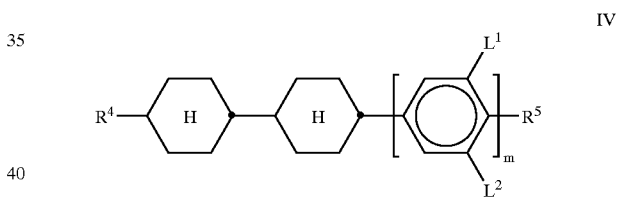

in which m is 0 or 1, $R^4$ is an alkenyl group having from 2 to 7 carbon atoms, $R^5$ is as defined for $R^a$ or, if m=1, is alternatively F, Cl, $CF_3$ or $OCF_3$, $L^1$ and $L^2$ are each, independently of one another, H or F.

Particularly preferred compounds of the formula IV are those in which $R^4$ is alkenyl having from 2 to 7 carbon atoms, in particular those of the following formulae:

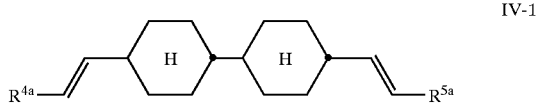

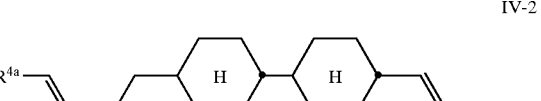

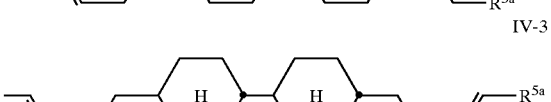

-continued

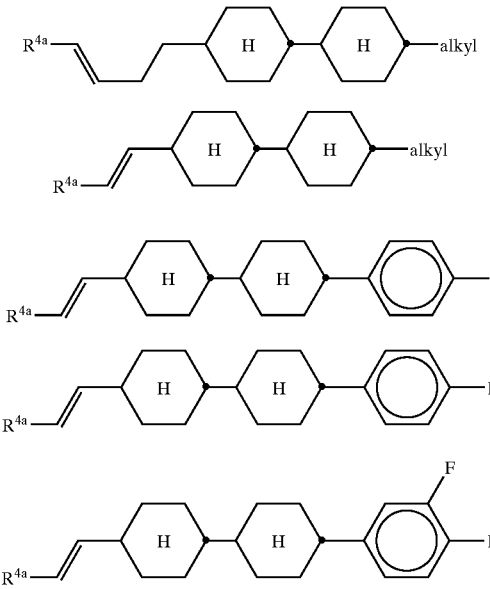

in which $R^{4a}$ and $R^{5a}$ are each, independently of one another, H, $CH_3$, $C_2H_5$ or n-$C_3H_7$, and alkyl is an alkyl group having from 1 to 7 carbon atoms.

Particular preference is given to TN and STN displays according to the invention in which the liquid-crystal mixture comprises at least one compound of the formula IV-1 and/or IV-3 in which $R^{4a}$ and $R^{5a}$ each have the same meaning, and displays in which the liquid-crystal mixture comprises at least one compound of the formula IV-5.

In a further preferred embodiment, the mixtures according to the invention comprise one or more compounds of the formula IV-6.

Component B preferably furthermore comprises compounds selected from the group consisting of the bicyclic compounds of the formulae V-1 to V-9

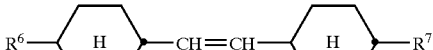

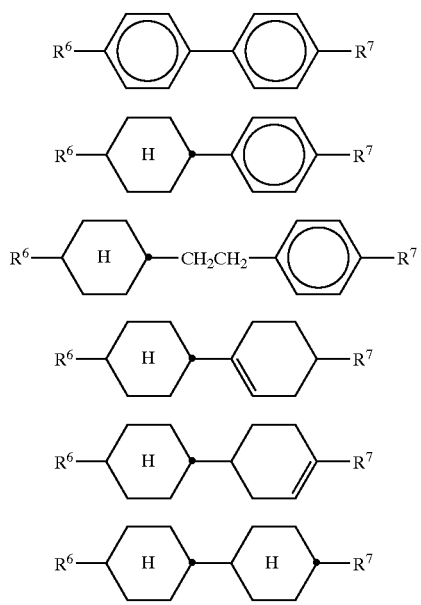

and/or one or more compounds selected from the group consisting of the tricyclic compounds of the formulae V-10 to V-27

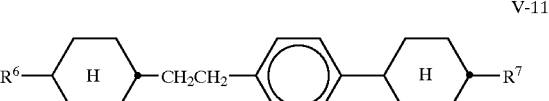

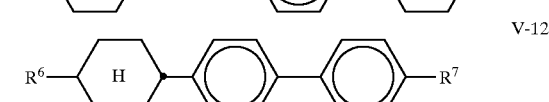

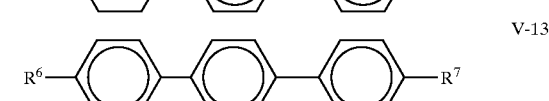

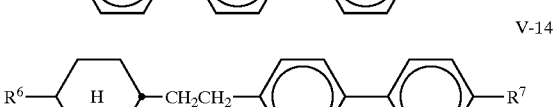

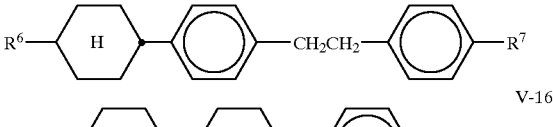

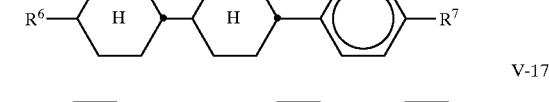

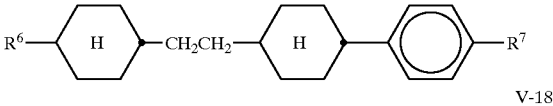

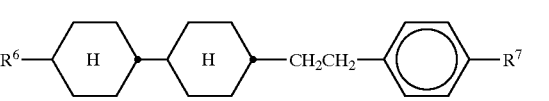

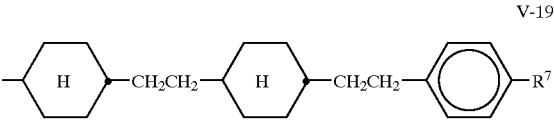

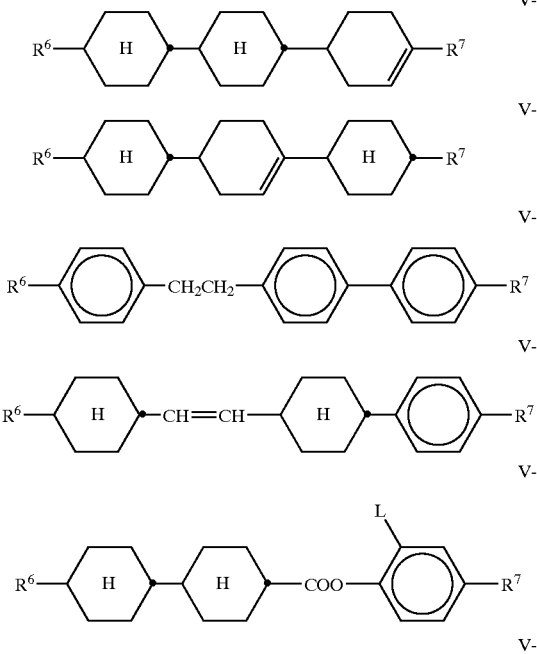

V-21
V-22
V-23
V-24
V-25
V-26
V-27 and/or one or more compounds selected from the group consisting of the tetracyclic compounds of the formulae V-28 to V-34

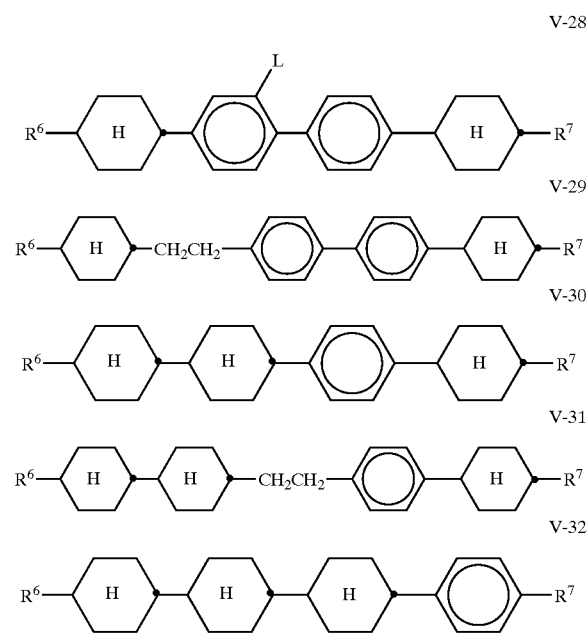

V-28
V-29
V-30
V-31
V-32

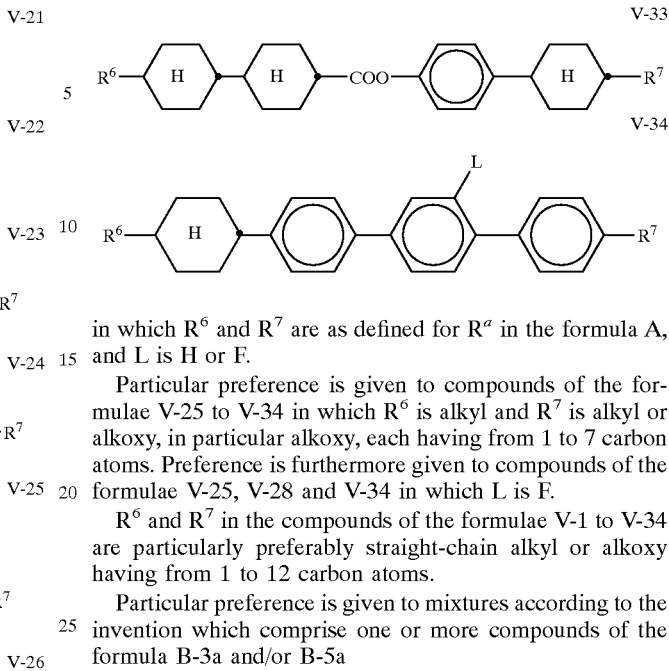

V-33
V-34 in which $R^6$ and $R^7$ are as defined for $R^a$ in the formula A, and L is H or F.

Particular preference is given to compounds of the formulae V-25 to V-34 in which $R^6$ is alkyl and $R^7$ is alkyl or alkoxy, in particular alkoxy, each having from 1 to 7 carbon atoms. Preference is furthermore given to compounds of the formulae V-25, V-28 and V-34 in which L is F.

$R^6$ and $R^7$ in the compounds of the formulae V-1 to V-34 are particularly preferably straight-chain alkyl or alkoxy having from 1 to 12 carbon atoms.

Particular preference is given to mixtures according to the invention which comprise one or more compounds of the formula B-3a and/or B-5a

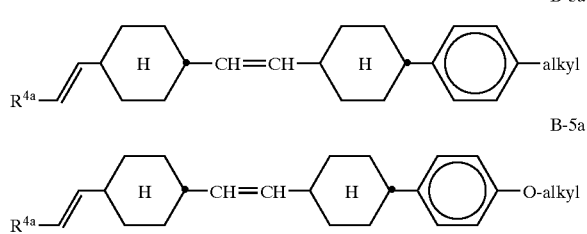

B-3a
B-5a

The mixtures preferably comprise 2–25% by weight, in particular 2–15% by weight, of compounds of the formula B-5a.

If desired, the liquid-crystalline mixtures may comprise an optically active component C in such an amount that the ratio between the layer thickness (separation of the outer plates) and the natural pitch of the chiral nematic liquid-crystal mixture is greater than 0.2. A multiplicity of chiral dopants, some of which are commercially available, is available to the person skilled in the art for the component, such as, for example, cholesteryl nonanoate, S-811, S-1011, S-2011, S-4011, and S-5011 from Merck KGaA, Darmstadt, and CB15 (BDH, Poole, UK). The choice of dopants is not crucial per se.

The proportion of the compounds of component C is preferably from 0 to 10%, in particular from 0 to 5%, particularly preferably from 0 to 3%.

The mixtures according to the invention may also, if desired, comprise up to 20% of one or more compounds having a dielectric anisotropy of less than −2 (component D).

If the mixtures comprise compounds of component D, these are preferably one or more compounds containing the structural unit 2,3-difluoro-1,4-phenylene, for example compounds as described in DE-A 38 07 801, 38 07 861, 38 07 863, 38 07 864 or 38 07 908. Particular preference is given to tolans containing this structural unit, as described in International Patent Application PCT/DE 88/00133.

Further known compounds of component D are, for example, derivatives of the 2,3-dicyanohydroquinones or cyclohexane derivatives containing the structural unit

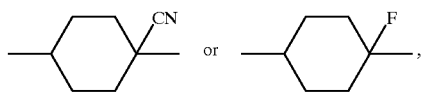

as described in DE-A 32 31 707 and DE-A 34 07 013.

The liquid-crystal displays according to the invention preferably contain no compounds of component D.

The term "alkenyl" in the definition of $R^a$, $R^b$, $R^2$, $R^3$, $R^4$, $R^5$, $R^6$ and $R^7$ covers straight-chain and branched alkenyl groups, in particular the straight-chain groups. Particularly preferred alkenyl groups are $C_2$–$C_7$-1E-alkenyl, $C_4$–$C_7$-3E-alkenyl, $C_5$–$C_7$-4-alkenyl, $C_6$–$C_7$-5-alkenyl and $C_7$-6-alkenyl, in particular $C_2$–$C_7$-1E-alkenyl, $C_4$–$C_7$-3E-alkenyl and $C_5$–$C_7$-4-alkenyl.

Examples of preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

Further preferred embodiments relate to liquid-crystal mixtures according to the invention which additionally comprise one or more, particularly preferably one, two or three, heterocyclic compounds of the formula Va and/or Vb

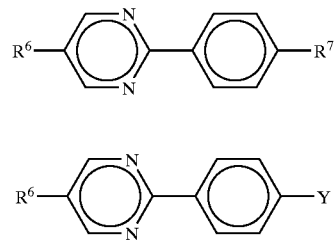

in which
$R^6$ and $R^7$ are as defined above,
and
Y is F or Cl,
where the proportion of the compounds from the group consisting of Va and Vb is preferably from 2 to 35%, in particular from 5 to 20%, additionally comprise one or more, particularly preferably one, two or three, tolan compounds of the formulae T2a, T2b and/or T2c

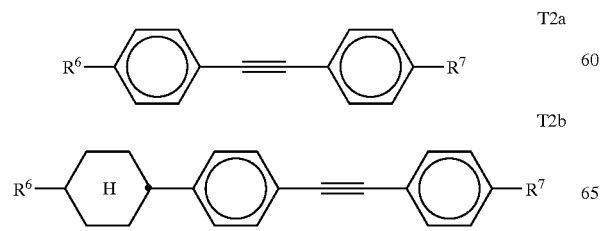

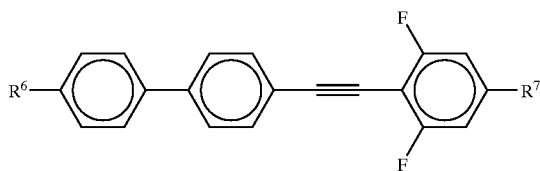

in which $R^6$ and $R^7$ are as defined above.

The proportion of the compounds from the group consisting of T2a, T2b and/or T2c is preferably from 2 to 20%, in particular from 4 to 12%. The mixture according to the invention preferably comprises two or three compounds of the formula T2a and/or T2b.

In particularly preferred embodiments, the mixtures comprise at least one compound of the formula A-2

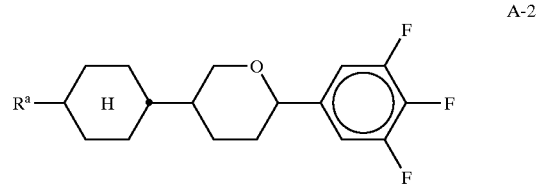

and at least one compound of the formula B-1

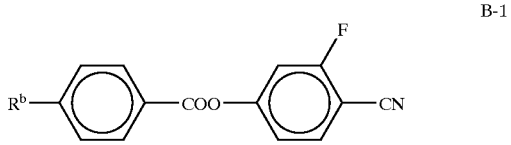

at least one compound of the formula Iij;

at least one tolan compound of the formula T2c;

at least two, in particular three, compounds of the formula A;

at least two, in particular three, compounds of the formula B;

at least one compound of the formula T2a and at least one compound of the formula T2b;

at least one compound of the formula VI

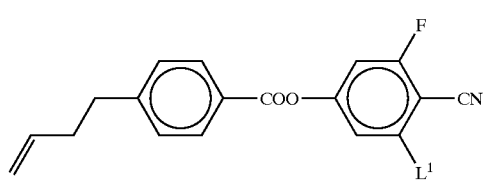

in which $L^1$ is H or F;

at least one compound of the formula VII

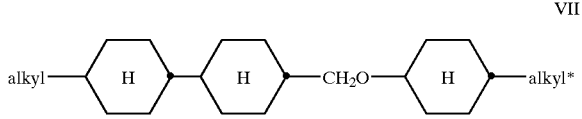

VII in which alkyl and alkyl* are each, independently of one another, an alkyl group having from 1 to 7 carbon atoms.

at least 2 to 30% by weight, preferably 2–25% by weight, in particular from 3 to 15% by weight, of compounds of the formula VII at least 2.5% by weight of the compounds of the formula IV-5;

5–30% by weight, preferably 10–25% by weight, of the compounds of the formula A;

3–30% by weight, preferably 3–20% by weight, of the compounds of the formula B;

at least three homologues of the compounds of the formula A, where $R^a$ is then preferably $C_2H_5$, n-$C_3H_7$ and n-$C_5H_{11}$.

Further particularly preferred embodiments relate to liquid-crystal mixtures which comprise a total of from three to six compounds of the formulae A and B, where the proportion of these compounds with respect to the mixture as a whole is from 25 to 65%, in particular from 30 to 55%, more than 20% of compounds of positive dielectric anisotropy, in particular having $\Delta\varepsilon \geq +12$.

The mixtures according to the invention are distinguished, in particular on use in TN and STN displays of high layer thicknesses, by very low total response times ($t_{tot}=t_{on}+t_{off}$).

The liquid-crystal mixtures used in the TN and STN cells according to the invention are dielectrically positive, with $\Delta\varepsilon \geq 1$. Particular preference is given to liquid-crystal mixtures with $\Delta\varepsilon \geq 3$, in particular with $\Delta\varepsilon \geq 5$.

The liquid-crystal mixtures according to the invention have favourable values for the threshold voltage $V_{10/0/20}$ and for the rotational viscosity $\gamma_1$. If the value for the optical path difference d·Δn is pre-specified, the value for the layer thickness d is determined by the optical anisotropy Δn. In particular at relatively high values for d·Δn, the use of liquid-crystal mixtures according to the invention having a relatively high value for the optical anisotropy is generally preferred, since the value for d can then be selected to be relatively small, which results in more favourable values for the response times. However, liquid-crystal displays according to the invention which contain liquid-crystal mixtures according to the invention with smaller values for Δn are also characterised by advantageous values for the response times.

The liquid-crystal mixtures according to the invention are furthermore characterised by advantageous values for the steepness of the electro-optical characteristic line, and can be operated with high multiplex rates, in particular at temperatures above 20° C. In addition, the liquid-crystal mixtures according to the invention have high stability and favourable values for the electrical resistance and the frequency dependence of the threshold voltage. The liquid-crystal displays according to the invention have a large working-temperature range and good angle dependence of the contrast.

The construction of the liquid-crystal display elements according to the invention from polarisers, electrode base plates and electrodes having a surface treatment such that the preferential alignment (director) of the liquid-crystal molecules in each case adjacent thereto is usually twisted by a value of from 160° to 720° from one electrode to the other corresponds to the usual structure for display elements of this type. The term "usual structure" here is broadly drawn and also covers all derivatives and modifications of the TN and STN cell, in particular also matrix display elements and display elements containing additional magnets.

The surface tilt angle at the two outer plates may be identical or different. Identical tilt angles are preferred. Preferred TN displays have pre-tilt angles between the longitudinal axis of the molecules at the surface of the outer plates and the outer plates of from 0° to 7°, preferably from 0.010 to 5°, in particular from 0.1 to 2°. In the STN displays, the pre-tilt angle is from 1° to 30°, preferably from 1° to 12° and in particular from 3° to 10°.

The twist angle of the TN mixture in the cell has a value of between 22.5° and 170°, preferably between 45° and 130° and in particular between 80° and 115°. The twist angle of the STN mixture in the cell from alignment layer to alignment layer has a value of between 100° and 600°, preferably between 170° and 300° and in particular between 180° and 270°.

The liquid-crystal mixtures which can be used in accordance with the invention are prepared in a manner which is conventional per se. In general, the desired amount of the components used in lesser amount are dissolved in the components making up the principal constituent, advantageously at elevated temperature. It is also possible to mix solutions of the components in an organic solvent, for example in acetone, chloroform or methanol, and to remove the solvent again, for example by distillation, after thorough mixing.

The dielectrics may also comprise further additives which are known to the person skilled in the art and are described in the literature. For example, 0–15% of pleochroic dyes, stabilisers, such as, for example, Tinuvin® from Ciba, antioxidants, UV absorbers, etc., may be added.

In the present application and in the examples below, the structures of the liquid-crystal compounds are indicated by means of acronyms, the transformation into chemical formulae taking place in accordance with Tables A and B. All radicals $C_nH_{2n+1}$ and $C_mH_{2m+1}$ are straight-chain alkyl radicals having n and m carbon atoms respectively. The alkenyl radicals have the trans-configuration. The coding in Table B is self-evident. In Table A, only the acronym for the parent structure is indicated. In individual cases, the acronym for the parent structure is followed, separated by a dash, by the code indicated in the table below for the substituents $R^{1*}$, $R^{2*}$, $L^{1*}$, $L^{2*}$ and $L^{3*}$.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German Application No. 10260517.3, filed Dec. 21, 2002 is hereby incorporated by reference.

| Code for $R^{1*}$, $R^{2*}$, $L^{1*}$, $L^{2*}$, $L^{3*}$ | $R^{1*}$ | $R^{2*}$ | $L^{1*}$ | $L^{2*}$ | $L^{3*}$ |
|---|---|---|---|---|---|
| nm | $C_nH_{2n+1}$ | $C_mH_{2m+1}$ | H | H | H |
| nOm | $OC_nH_{2n+1}$ | $C_mH_{2m+1}$ | H | H | H |
| nO.m | $C_nH_{2n+1}$ | $OC_mH_{2m+1}$ | H | H | H |
| n | $C_nH_{2n+1}$ | CN | H | H | H |
| nN.F | $C_nH_{2n+1}$ | CN | H | H | F |
| nN.F.F | $C_nH_{2n+1}$ | CN | H | F | F |
| nF | $C_nH_{2n+1}$ | F | H | H | H |
| nOF | $OC_nH_{2n+1}$ | F | H | H | H |
| nF.F | $C_nH_{2n+1}$ | F | H | H | F |
| nmF | $C_nH_{2n+1}$ | $C_mH_{2m+1}$ | F | H | H |
| nOCF$_3$ | $C_nH_{2n+1}$ | OCF$_3$ | H | H | H |
| n-Vm | $C_nH_{2n+1}$ | —CH=CH—$C_mH_{2m+1}$ | H | H | H |
| nV-Vm | $C_nH_{2n+1}$—CH=CH— | —CH=CH—$C_mH_{2m+1}$ | H | H | H |
| n.F.F.F | $C_nH_{2n+1}$ | F | H | F | F |

The displays, in particular TN-, STN- and IPS displays, preferably contain liquid-crystalline mixtures composed of one or more compounds from Tables A and B.

TABLE A ($L^{1*}$, $L^{2*}$, $L^{3*}$ = H or F)

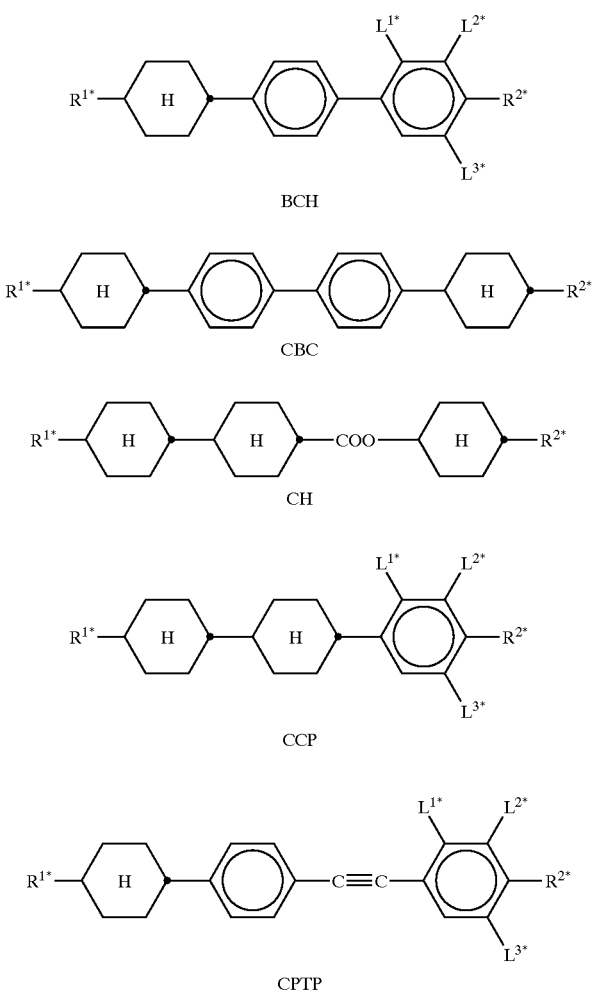

BCH

CBC

CH

CCP

CPTP

TABLE A-continued
($L^{1*}$, $L^{2*}$, $L^{3*}$ = H or F)
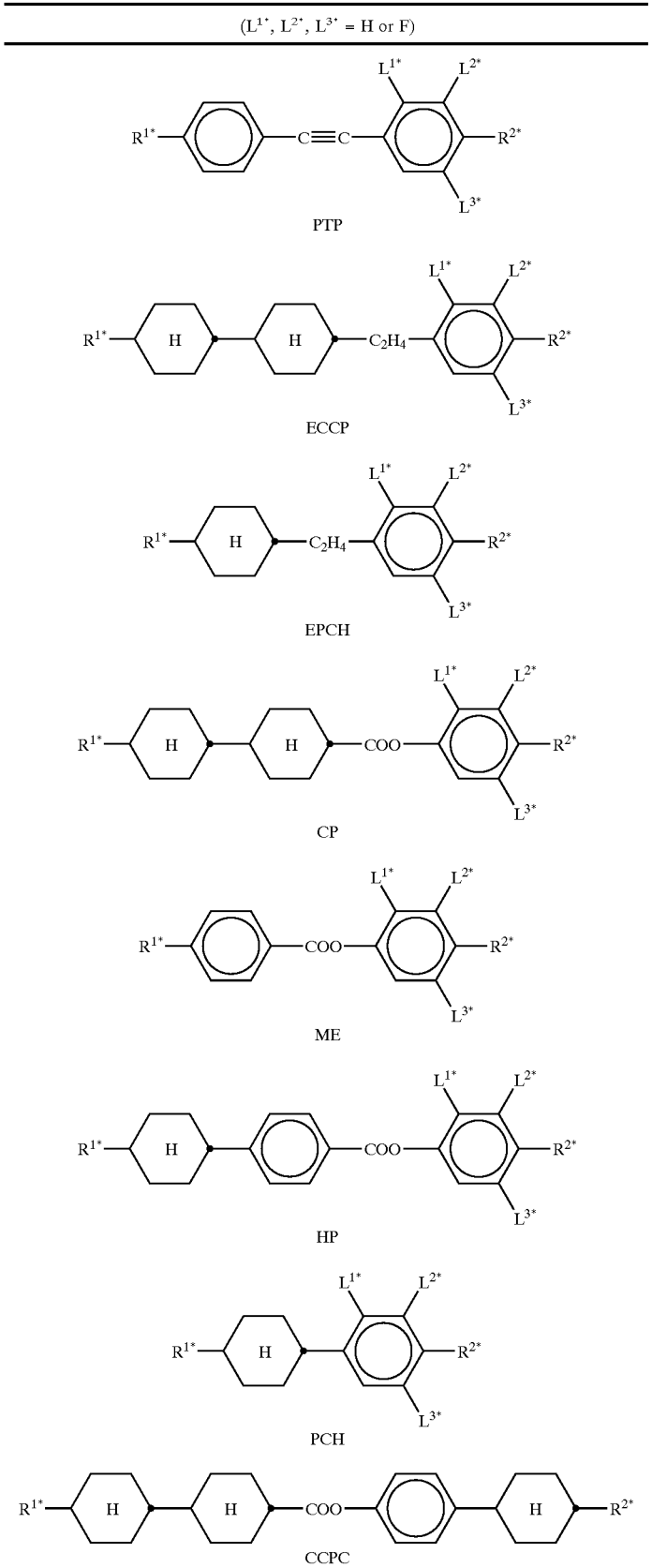

TABLE A-continued
(L¹*, L²*, L³* = H or F)
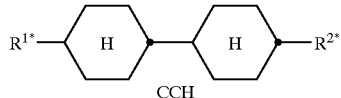
CCH
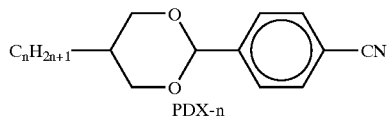
PDX-n
TABLE B
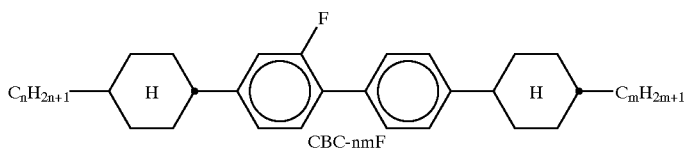
CBC-nmF
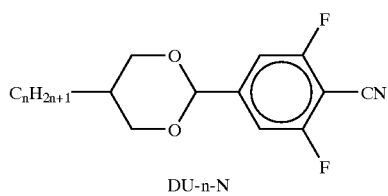
DU-n-N
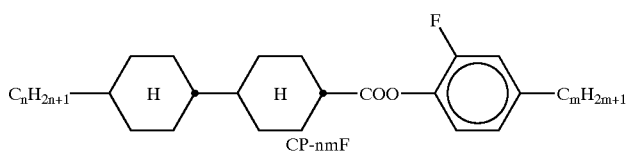
CP-nmF
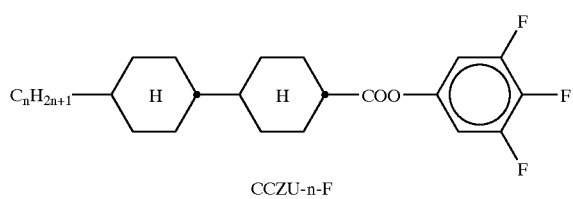
CCZU-n-F
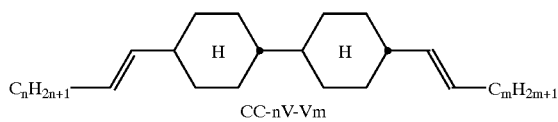
CC-nV-Vm
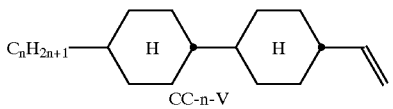
CC-n-V
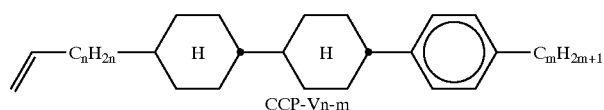
CCP-Vn-m
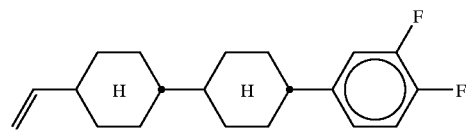

TABLE B-continued
CCG-V-F
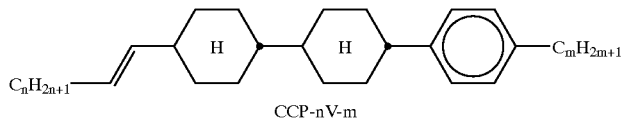
CCP-nV-m
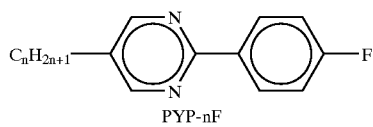
PYP-nF
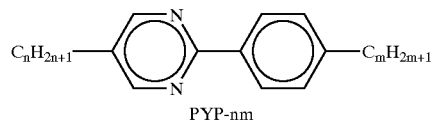
PYP-nm
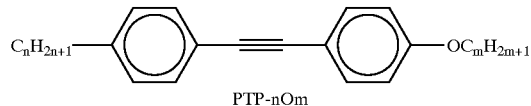
PTP-nOm
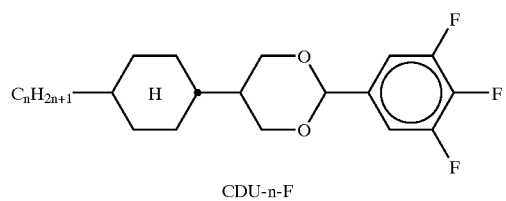
CDU-n-F
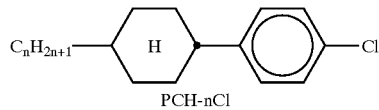
PCH-nCl
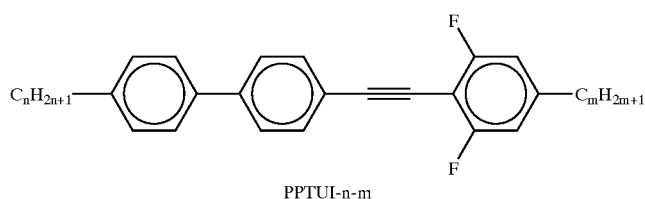
PPTUI-n-m
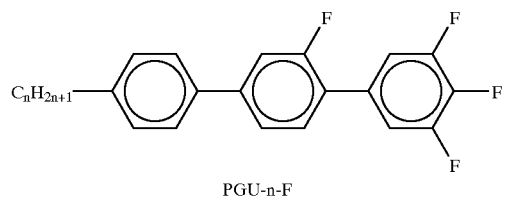
PGU-n-F
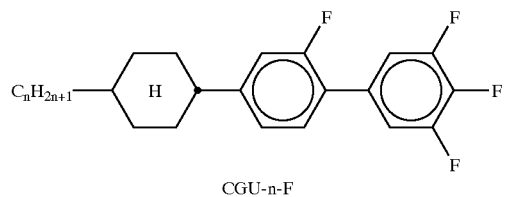
CGU-n-F TABLE B-continued
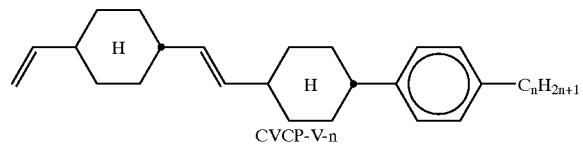
CVCP-V-n
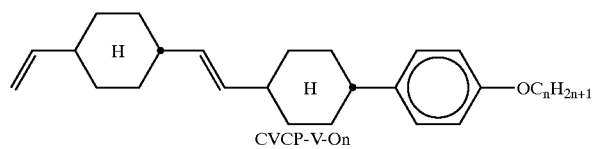
CVCP-V-On
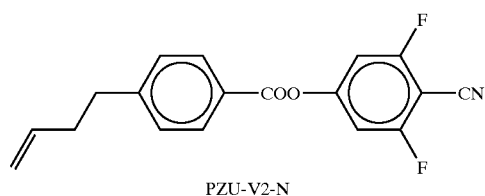
PZU-V2-N
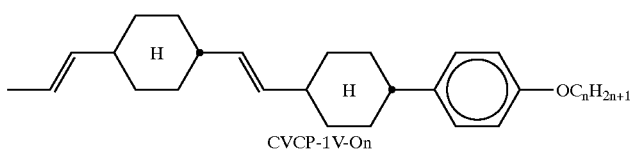
CVCP-1V-On
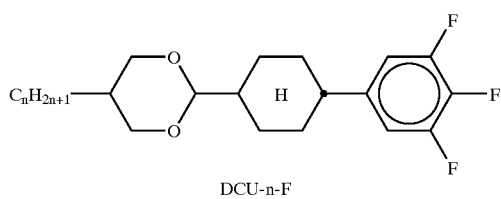
DCU-n-F
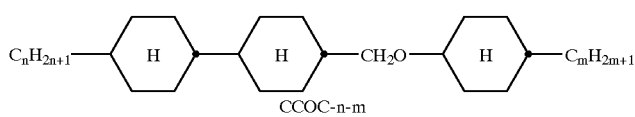
CCOC-n-m
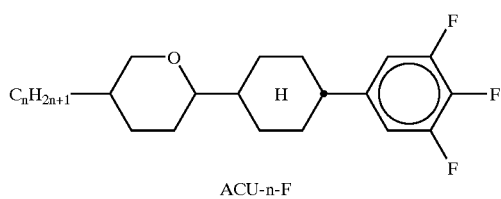
ACU-n-F
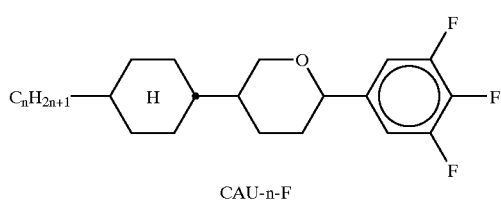
CAU-n-F
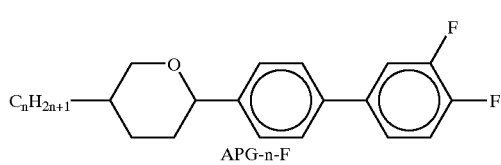
APG-n-F

TABLE B-continued
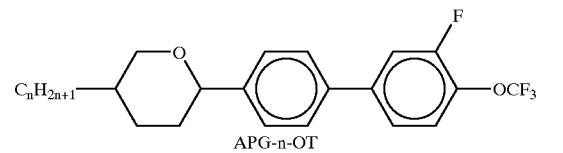
APG-n-OT
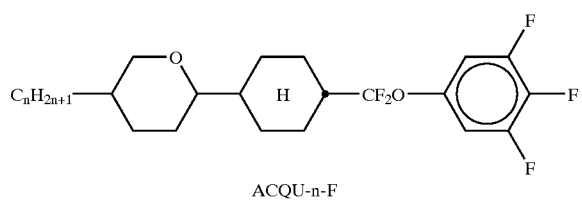
ACQU-n-F
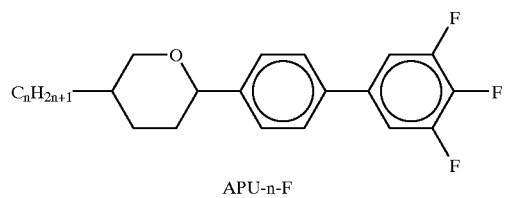
APU-n-F
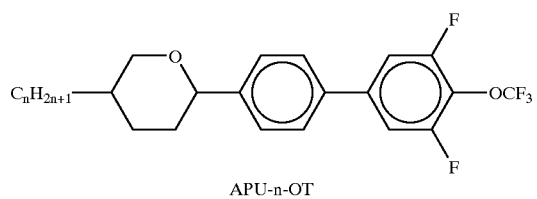
APU-n-OT
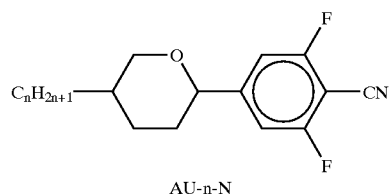
AU-n-N
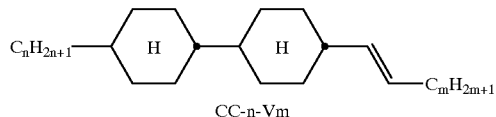
CC-n-Vm
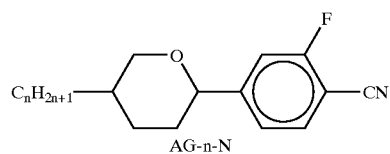
AG-n-N
TABLE C
Table C shows dopants which can be added to the mixtures according to the invention. The mixtures preferably comprise from 0.01 to 10% by weight of dopant.
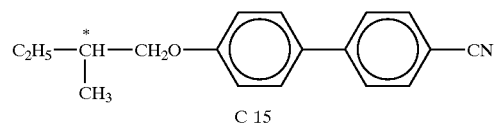
C 15

TABLE C-continued
Table C shows dopants which can be added to the mixtures according to the invention.
The mixtures preferably comprise from 0.01 to 10% by weight of dopant.
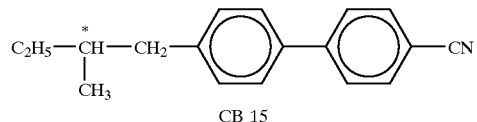
CB 15
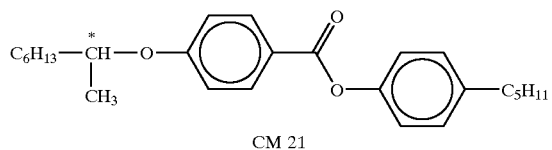
CM 21
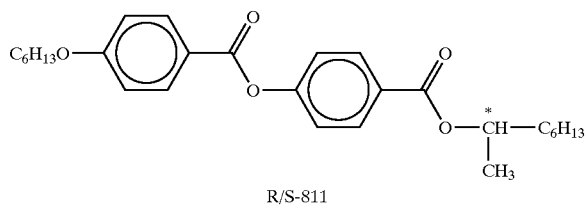
R/S-811
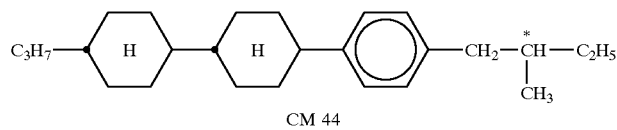
CM 44
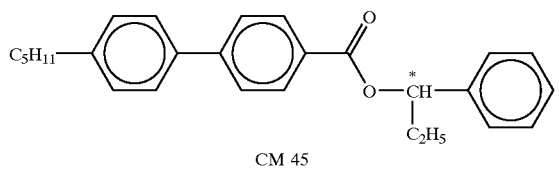
CM 45
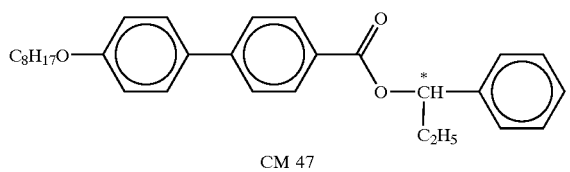
CM 47
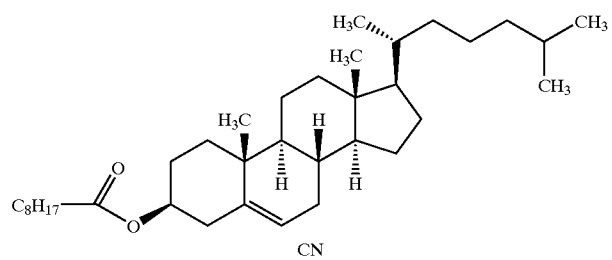
CN
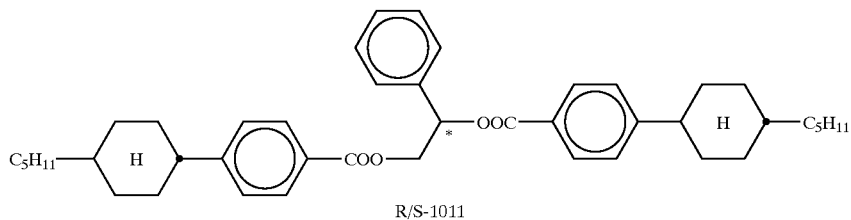
R/S-1011

TABLE C-continued

Table C shows dopants which can be added to the mixtures according to the invention.
The mixtures preferably comprise from 0.01 to 10% by weight of dopant.

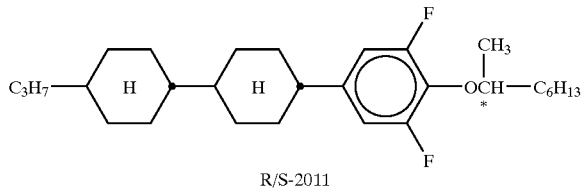

R/S-2011

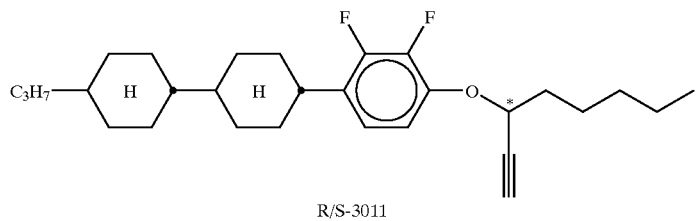

R/S-3011

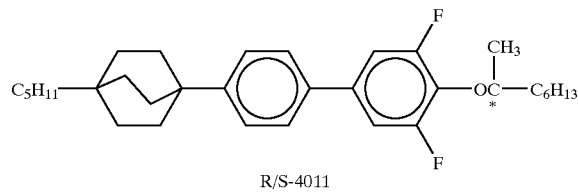

R/S-4011

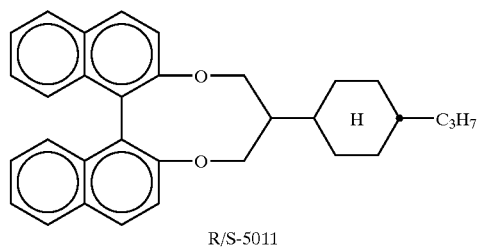

R/S-5011

TABLE D

Stabilisers which can be added, for example, to the mixtures according to the invention are shown below:

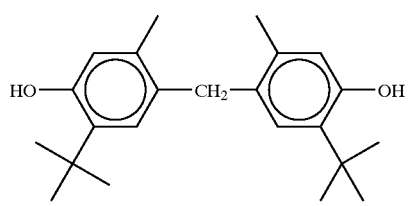

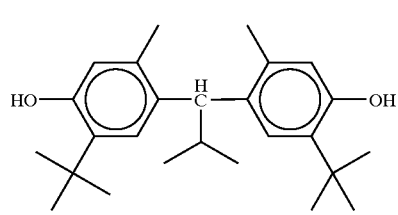

TABLE D-continued

Stabilisers which can be added, for example, to the mixtures according to the invention are shown below:

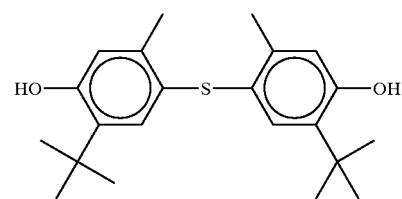

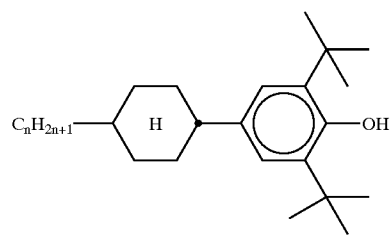

TABLE D-continued
Stabilisers which can be added, for example, to the mixtures according to the invention are shown below:
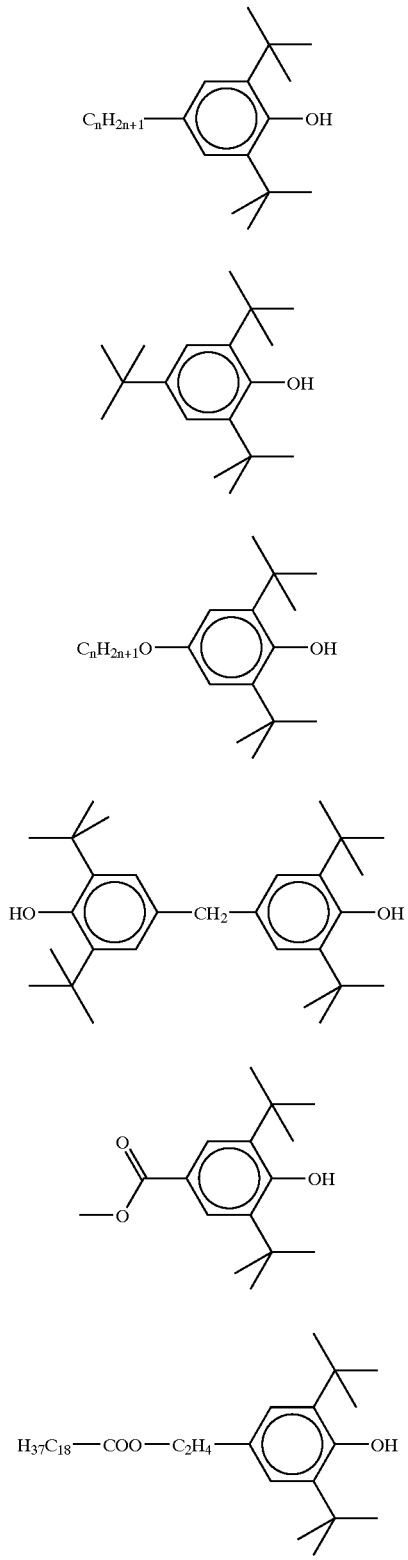
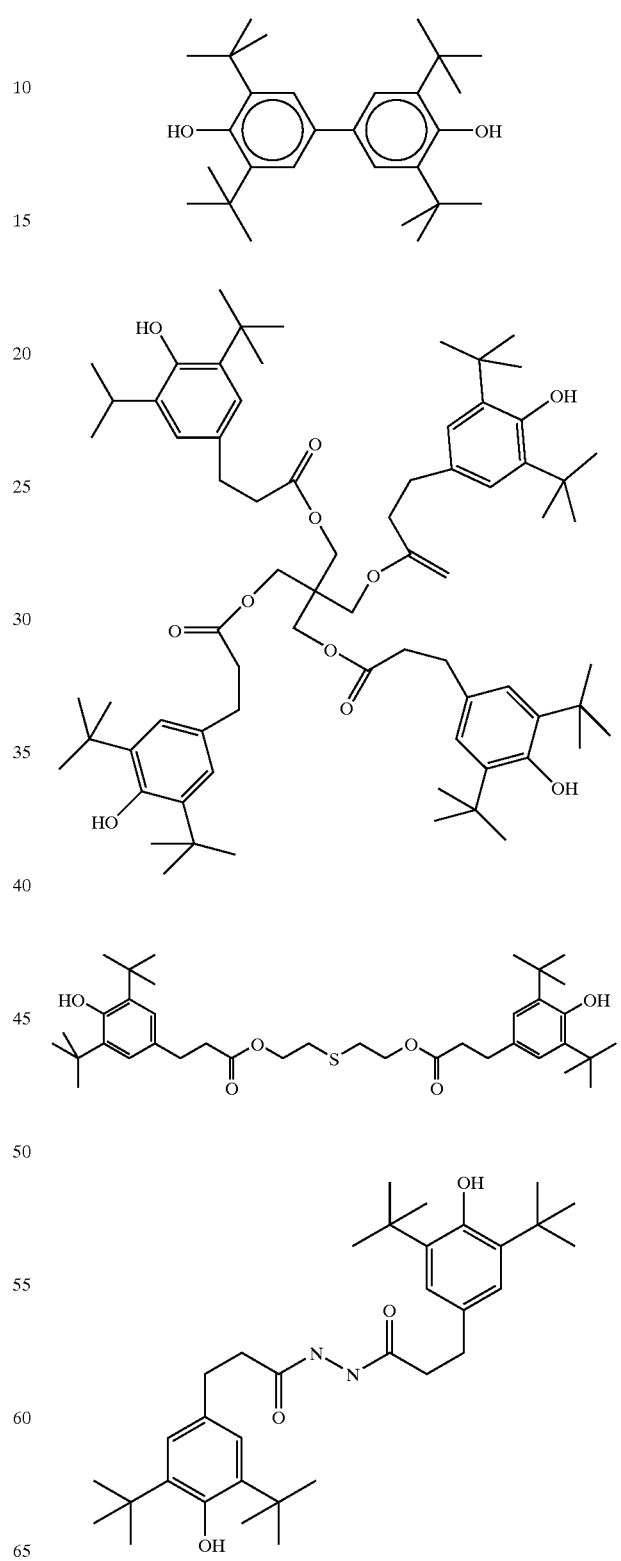

TABLE D-continued
Stabilisers which can be added, for example, to the mixtures according to the invention are shown below:
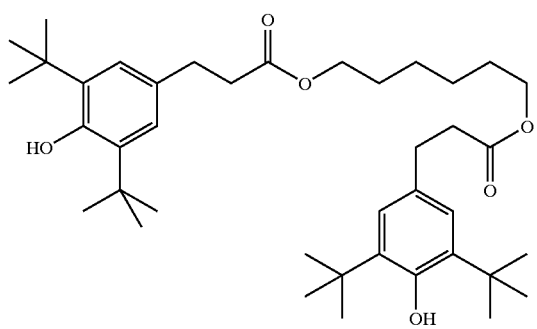
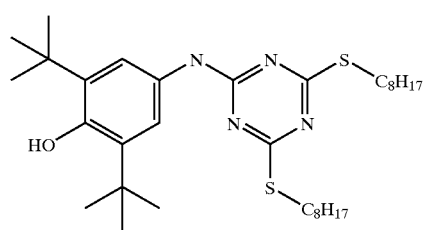
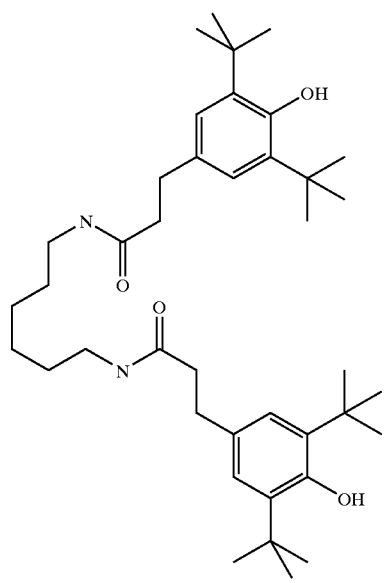
TABLE D-continued
Stabilisers which can be added, for example, to the mixtures according to the invention are shown below:
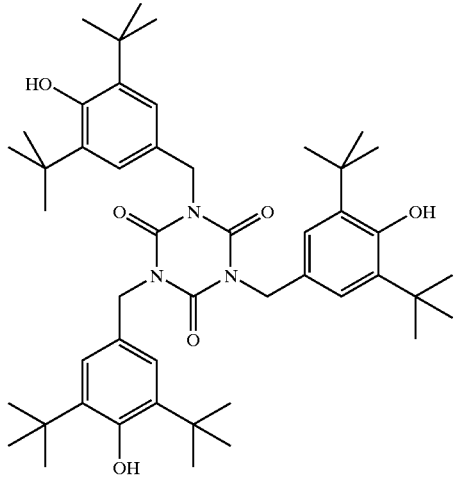
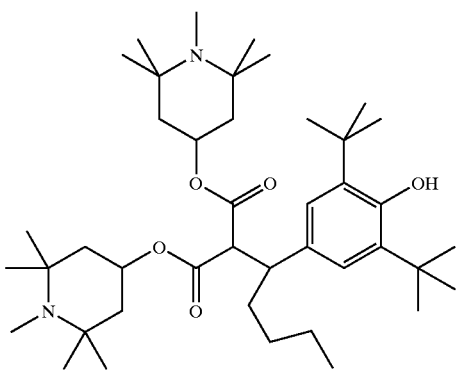
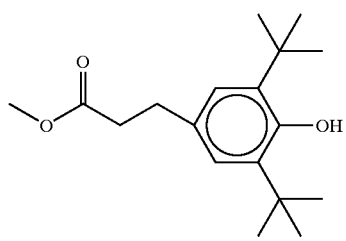
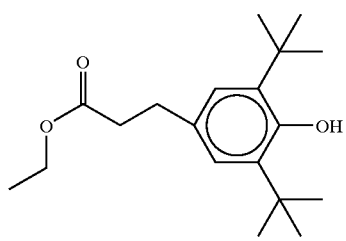
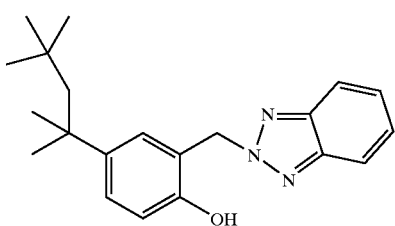

TABLE D-continued
Stabilisers which can be added, for example, to the mixtures according to the invention are shown below:
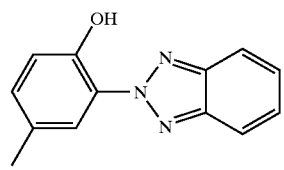
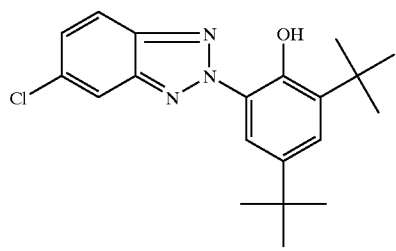
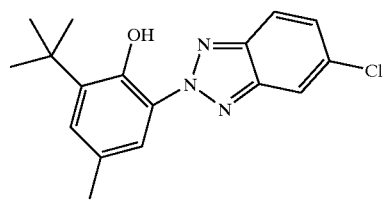
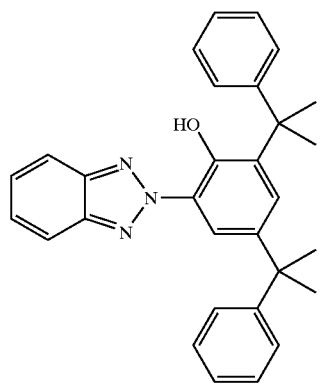
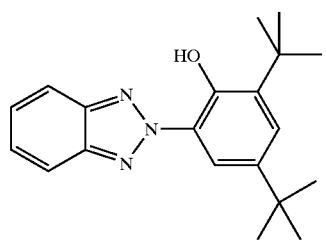
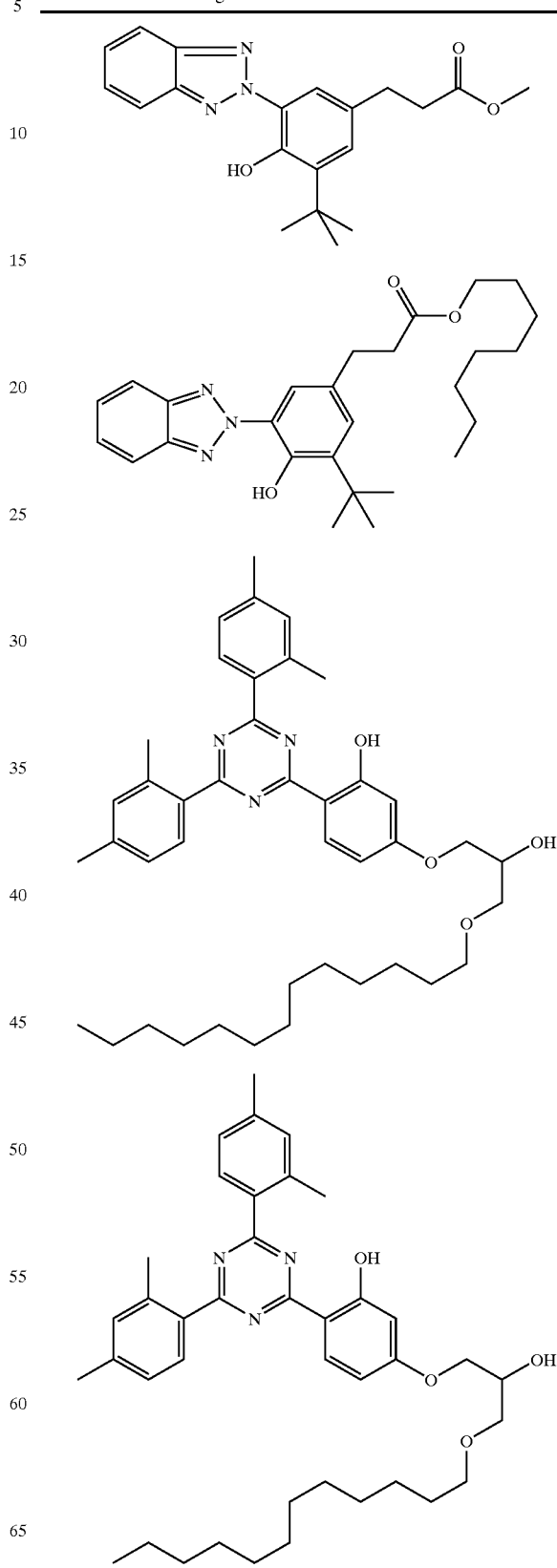

TABLE D-continued

Stabilisers which can be added, for example, to the mixtures according to the invention are shown below:

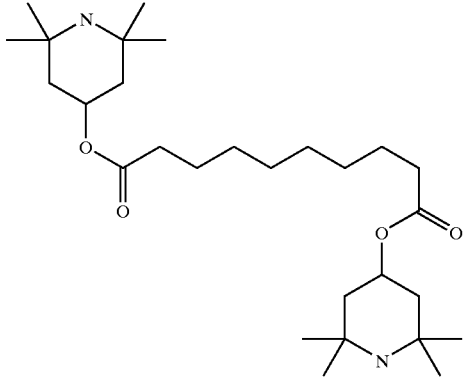

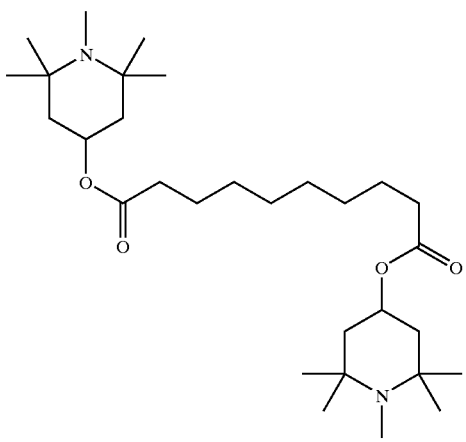

The following examples are intended to illustrate the invention without re-resenting a limitation. The following abbreviations are used:

cl.p. clearing point (nematic-isotropic phase transition temperature),
S-N smectic-nematic phase transition temperature,
$v_{20}$ flow viscosity (mm²/s, unless stated otherwise, at 20° C.),
$\Delta n$ optical anisotropy (589 nm, 20° C.)
$\Delta\epsilon$ dielectric anisotropy (1 kHz, 20° C.)
$\gamma_1$ rotational viscosity (mPa·s at 20° C.)
steep characteristic line steepness=$(V_{90}/V_{10}-1) \cdot 100$ [%]
$V_{10}$ threshold voltage=characteristic voltage at a relative contrast of 10%,
$V_{90}$ characteristic voltage at a relative contrast of 90%,
$t_{ave}$ $$\frac{t_{on} + t_{off}}{2} \text{ (average response time)}$$

$t_{on}$ time from switching on until 90% of the maximum contrast is reached,
$t_{off}$ time from switching off until 10% of the maximum contrast is reached,
mux multiplex rate
$t_{store}$ low temperature storage stability in hours (−20° C., −30° C., −40° C.)

Above and below, all temperatures are given in ° C. The percentages are percent by weight. All values relate to 20° C., unless stated otherwise. The displays are addressed, unless stated otherwise, without multiplexing.

EXAMPLE 1

| | | | |
|---|---|---|---|
| ME2N.F | 6.00% | Clearing point [° C.]: | 95.0 |
| ME3N.F | 7.00% | $\Delta n$ [589 nm, 20° C.]: | 0.1419 |
| ME4N.F | 11.00% | $\Delta\epsilon$ [1 kHz, 20° C.]: | 28.3 |
| ME5N.F | 10.00% | $\gamma_1$ [20° C.; mPa·s]: | 334 |
| CGU-2-F | 8.00% | Twist [°]: | 240 |
| CGU-3-F | 8.00% | | |
| CCZU-2-F | 4.00% | | |
| CCZU-3-F | 10.50% | | |
| CCZU-5-F | 4.00% | | |
| CCPC-33 | 2.00% | | |
| CCPC-34 | 2.00% | | |
| CBC-33F | 5.00% | | |
| CBC-53F | 5.00% | | |
| CBC-55F | 5.00% | | |
| CPTP-301 | 3.50% | | |
| APU-3-F | 9.00% | | |

EXAMPLE 2

| | | | |
|---|---|---|---|
| PCH-3N.F.F | 12.00% | Clearing point [° C.]: | 106.0 |
| ME2N.F | 2.00% | $\Delta n$ [589 nm, 20° C.]: | 0.1388 |
| ME3N.F | 3.00% | $\Delta\epsilon$ [1 kHz, 20° C.]: | 11.9 |
| CGU-2-F | 5.00% | $\gamma_1$ [20° C.; mPa·s]: | 195 |
| CGU-3-F | 5.00% | Twist [°]: | 240 |
| APU-3-F | 7.00% | | |
| CCP-2F.F.F | 4.00% | | |
| CAU-3-F | 4.00% | | |
| CC-5-V | 2.00% | | |
| CCP-V-1 | 9.00% | | |
| CCP-V2-1 | 5.00% | | |
| CCG-V-F | 8.00% | | |
| CVCP-1V-O1 | 4.00% | | |
| PTP-102 | 4.00% | | |
| PTP-201 | 4.00% | | |
| PTP-301 | 4.00% | | |
| PTP-302 | 3.00% | | |
| CCPC-33 | 5.00% | | |
| CCPC-34 | 5.00% | | |
| CCPC-35 | 5.00% | | |

EXAMPLE 3

| | | | |
|---|---|---|---|
| PCH-3N.F.F | 8.00% | Clearing point [° C.]: | 79.0 |
| ME2N.F | 10.00% | $\Delta n$ [589 nm, 20° C.]: | 0.1314 |
| ME3N.F | 10.00% | $\Delta\epsilon$ [1 kHz, 20° C.]: | 45.0 |
| ME4N.F | 11.00% | $\gamma_1$ [20° C.; mPa·s]: | 397 |
| ME5N.F | 10.00% | Twist [°]: | 240 |
| HP-3N.F | 5.00% | | |
| HP-4N.F | 5.00% | | |
| HP-5N.F | 4.00% | | |
| CCP-2F.F.F | 5.00% | | |
| CCP-3F.F.F | 5.00% | | |
| CCP-5F.F.F | 5.00% | | |
| CCPC-33 | 4.00% | | |
| CCPC-34 | 4.00% | | |
| CCPC-35 | 4.00% | | |
| ACU-3-F | 10.00% | | |

EXAMPLE 4

| | | | |
|---|---|---|---|
| PCH-3N.F.F | 8.00% | Clearing point [° C.]: | 79.0 |
| ME2N.F | 10.00% | Δn [589 nm, 20° C.]: | 0.1312 |
| ME3N.F | 10.00% | Δε [1 kHz, 20° C.]: | 45.0 |
| ME4N.F | 11.00% | γ₁ [20° C.; mPa · s]: | 385 |
| ME5N.F | 10.00% | | |
| HP-3N.F | 5.00% | | |
| HP-4N.F | 5.00% | | |
| HP-5N.F | 4.00% | | |
| CCP-2F.F.F | 5.00% | | |
| CCP-3F.F.F | 6.00% | | |
| CCP-5F.F.F | 5.00% | | |
| CCPC-33 | 4.00% | | |
| CCPC-34 | 3.00% | | |
| CCPC-35 | 4.00% | | |
| ACQU-3-F | 10.00% | | |

EXAMPLE 5

| | | | |
|---|---|---|---|
| PCH-3N.F.F | 8.00% | Clearing point [° C.]: | 79.5 |
| ME2N.F | 10.00% | Δn [589 nm, 20° C.]: | 0.1326 |
| ME3N.F | 10.00% | Δε [1 kHz, 20° C.]: | 44.7 |
| ME4N.F | 11.00% | γ₁ [20° C.; mPa · s]: | 399 |
| ME5N.F | 10.00% | | |
| HP-3N.F | 5.00% | | |
| HP-4N.F | 5.00% | | |
| HP-5N.F | 4.00% | | |
| CCP-2F.F.F | 5.00% | | |
| CCP-3F.F.F | 6.00% | | |
| CCP-5F.F.F | 5.00% | | |
| CCPC-33 | 3.00% | | |
| CCPC-34 | 4.00% | | |
| CCPC-35 | 4.00% | | |
| CAU-3-F | 10.00% | | |

EXAMPLE 6

| | | | |
|---|---|---|---|
| PCH-3N.F.F | 8.00% | Clearing point [° C.]: | 80.0 |
| ME2N.F | 10.00% | Δn [589 nm, 20° C.]: | 0.1389 |
| ME3N.F | 10.00% | Δε [1 kHz, 20° C.]: | 45.2 |
| ME4N.F | 11.00% | γ₁ [20° C.; mPa · s]: | 403 |
| ME5N.F | 10.00% | | |
| HP-3N.F | 5.00% | | |
| HP-4N.F | 5.00% | | |
| HP-5N-F | 4.00% | | |
| CCP-2F.F.F | 5.00% | | |
| CCP-3F.F.F | 5.00% | | |
| CCP-5F.F.F | 5.00% | | |
| CCPC-33 | 4.00% | | |
| CCPC-34 | 4.00% | | |
| CCPC-35 | 4.00% | | |
| APU-3-F | 10.00% | | |

EXAMPLE 7

| | | | |
|---|---|---|---|
| PCH-3N.F.F | 8.00% | Clearing point [° C.]: | 79.0 |
| ME2N.F | 10.00% | Δn [589 nm, 20° C.]: | 0.1382 |
| ME3N.F | 10.00% | Δε [1 kHz, 20° C.]: | 46.0 |
| ME4N.F | 11.00% | γ₁ [20° C.; mPa · s]: | 406 |
| ME5N.F | 10.00% | | |
| HP-3N.F | 5.00% | | |
| HP-4N.F | 5.00% | | |
| HP-5N.F | 4.00% | | |
| CCP-2F.F.F | 5.00% | | |
| CCP-3F.F.F | 6.00% | | |
| CCP-5F.F.F | 5.00% | | |
| CCPC-33 | 3.00% | | |
| CCPC-34 | 4.00% | | |
| CCPC-35 | 4.00% | | |
| APU-3-OT | 10.00% | | |

EXAMPLE 8

| | | | |
|---|---|---|---|
| PCH-3N.F.F | 8.00% | Clearing point [° C.]: | 79.0 |
| ME2N.F | 10.00% | Δn [589 nm, 20° C.]: | 0.1377 |
| ME3N.F | 10.00% | Δε [1 kHz, 20° C.]: | 45.1 |
| ME4N.F | 11.00% | γ₁ [20° C.; mPa · s]: | 391 |
| ME5N.F | 10.00% | | |
| HP-3N.F | 5.00% | | |
| HP-4N.F | 5.00% | | |
| HP-5N.F | 4.00% | | |
| CCP-2F.F.F | 5.00% | | |
| CCP-3F.F.F | 7.50% | | |
| CCP-5F.F.F | 5.00% | | |
| CCPC-33 | 3.00% | | |
| CCPC-34 | 3.50% | | |
| CCPC-35 | 3.00% | | |
| APG-3-OT | 10.00% | | |

EXAMPLE 9

| | | | |
|---|---|---|---|
| ME2N.F | 3.00% | Clearing point [° C.]: | 78.0 |
| PZU-V2-N | 5.00% | Δn [589 nm, 20° C.]: | 0.1078 |
| AU-3-N | 7.00% | Δε [1 kHz, 20° C.]: | 10.9 |
| PGU-2-F | 9.00% | γ₁ [20° C.; mPa · s]: | 85 |
| PGU-3-F | 6.00% | | |
| CCP-3OCF₃ | 8.00% | | |
| CCP-4OCF₃ | 2.00% | | |
| CC-3-V1 | 12.00% | | |
| CC-5-V | 14.00% | | |
| PCH-302 | 8.00% | | |
| CCP-V-1 | 15.00% | | |
| CCP-V2-1 | 11.00% | | |

EXAMPLE 10

| | | | |
|---|---|---|---|
| ME2N.F | 3.00% | Clearing point [° C.]: | 78.0 |
| PZU-V2-N | 5.00% | Δn [589 nm, 20° C.]: | 0.1075 |
| AG-3-N | 9.00% | Δε [1 kHz, 20° C.]: | 10.8 |
| PGU-2-F | 9.50% | γ₁ [20° C.; mPa · s]: | 87 |
| PGU-3-F | 5.00% | | |
| CCP-3OCF₃ | 8.00% | | |
| CCP-4OCF₃ | 4.00% | | |
| CC-3-V1 | 12.00% | | |
| CC-5-V | 15.00% | | |
| PCH-302 | 5.50% | | |
| CCP-V-1 | 15.00% | | |
| CCP-V2-1 | 9.00% | | |

EXAMPLE 11

| | | | |
|---|---|---|---|
| CCP-2OCF₃ | 7.00% | Clearing point [° C.]: | 75.0 |
| CCP-3OCF₃ | 7.00% | Δn [589 nm, 20° C.]: | 0.0750 |
| PDX-3 | 6.00% | Δε [1 kHz, 20° C.]: | 9.2 |

-continued

| | | | |
|---|---|---|---|
| PDX-4 | 4.00% | γ₁ [20° C.; mPa · s]: | 95 |
| ME2N.F | 2.50% | | |
| CCZU-2-F | 7.00% | | |
| CCZU-3-F | 15.00% | | |
| CH-33 | 1.50% | | |
| CH-35 | 2.00% | | |
| CH-43 | 2.00% | | |
| CC-5-V | 18.00% | | |
| CC-3-V1 | 11.00% | | |
| PCH-302 | 2.50% | | |
| ACU-2-F | 7.00% | | |
| ACU-3-F | 7.50% | | |

EXAMPLE 12

| | | | |
|---|---|---|---|
| ACU-2-F | 10.00% | Clearing point [° C.]: | 73.5 |
| ACQU-3-F | 11.00% | Δn [589 nm, 20° C.]: | 0.0782 |
| CCP-20CF₃ | 7.00% | Δε [1 kHz, 20° C.]: | 18.4 |
| CCP-30CF₃ | 8.00% | γ₁ [20° C.; mPa · s]: | 137 |
| CP-30CF₃ | 7.00% | | |
| CP-50CF₃ | 7.00% | | |
| DU-3-N | 12.50% | | |
| ME2N.F | 3.00% | | |
| ME3N.F | 2.00% | | |
| CCZU-2-F | 4.00% | | |
| CCZU-3-F | 15.00% | | |
| CCZU-4-F | 6.00% | | |
| CC-3-V1 | 2.50% | | |
| CCH-35 | 5.00% | | |

EXAMPLE 13

| | | | |
|---|---|---|---|
| ACU-2-F | 9.00% | Clearing point [° C.]: | 70.0 |
| ACU-3-F | 9.00% | Δn [589 nm, 20° C.]: | 0.0754 |
| ACQU-3-F | 9.00% | Δε [1 kHz, 20° C.]: | 10.1 |
| CCP-20CF₃ | 3.00% | γ₁ [20° C.; mPa · s]: | 83 |
| CCP-30CF₃ | 8.00% | | |
| CP-30CF₃ | 7.00% | | |
| CP-50CF₃ | 6.00% | | |
| PCH-3N.F.F | 10.00% | | |
| ME2N.F | 4.00% | | |
| ME3N.F | 2.00% | | |
| CCZU-2-F | 4.00% | | |
| CCZU-3-F | 15.00% | | |
| CCZU-5-F | 3.00% | | |
| CC-5-V | 11.00% | | |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A liquid-crystalline medium comprising one or more compounds of formula A

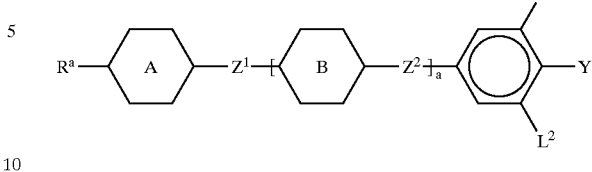

and at least one compound of formula B

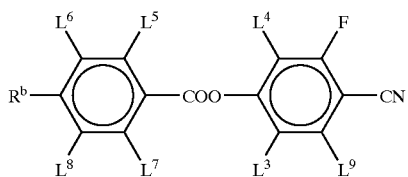

in which $R^a$ and $R^b$ are each, independently of one another, H or an alkyl radical having from 1 to 12 carbon atoms which is unsubstituted, mono substituted by CN or $CF_3$ or at least monosubstituted by halogen, and in which one or more $CH_2$ groups are each, independently of one another, optionally replaced by —O—, —S—,

—CH=CH—, —C≡C—, —CO—, —CO—O—, —O—CO— or —O—CO—O— in such a way that O atoms are not linked directly to one another,

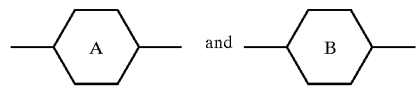

are each, independently of one another,

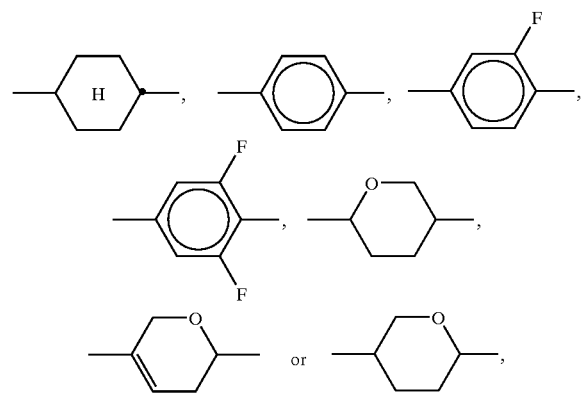

and at least one ring is

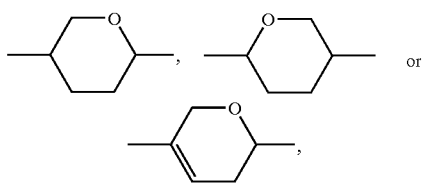

$Z^1$ and $Z^2$ are each, independently of one another, —CH$_2$CH$_2$—, —(CH$_2$)$_4$—, —CH$_2$O—, —OCH$_2$—, —CF$_2$O—, —OCF$_2$—, —C≡C—, —CF=CF—, —CH=CH—, —COO—, —CH$_2$—, —(CH$_2$)$_3$— or a single bond, a is 0 is 1, $L^1$ to $L^9$ to are each, independently of one another, H or F, and Y is F, Cl, SF$_5$, NCS, SCN, CN, OCN, or a monohalogenated or polyhalogenated alkyl, alkoxy, alkenyl or alkenyloxy radical, in each case having up to 5 carbon atoms.

2. A liquid-crystalline medium according to claim 1, wherein said medium contains at least one compound of formulae A-1 to A-56

A-1
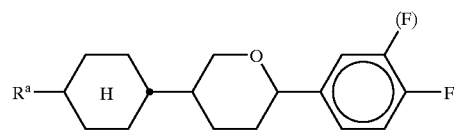

A-2
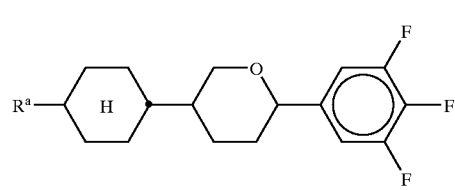

A-3
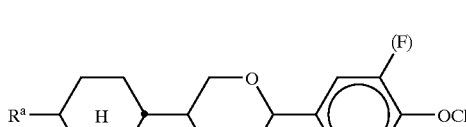

A-4
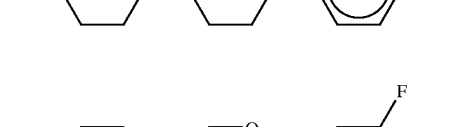

A-5
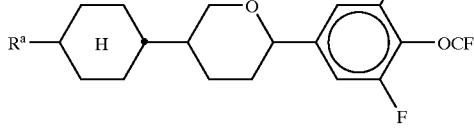

A-6
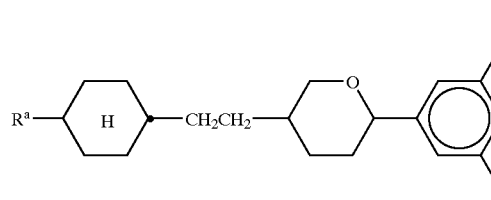

-continued

A-6
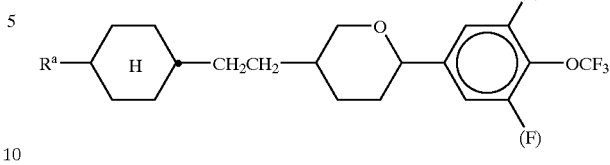

A-7
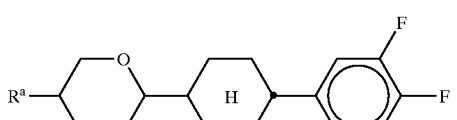

A-8
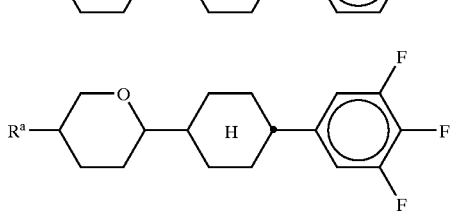

A-9
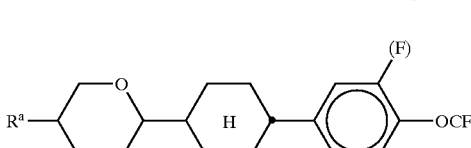

A-10
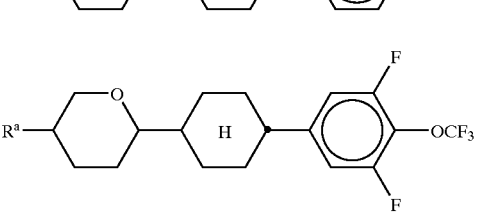

A-11
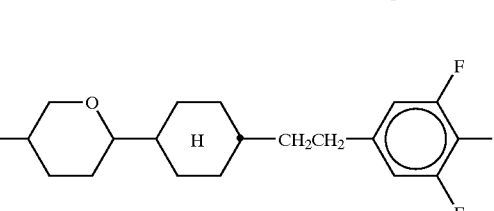

A-12
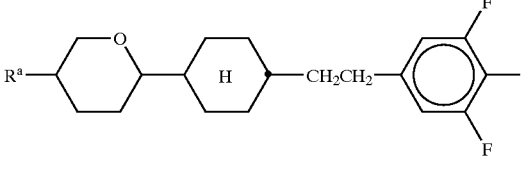

A-13
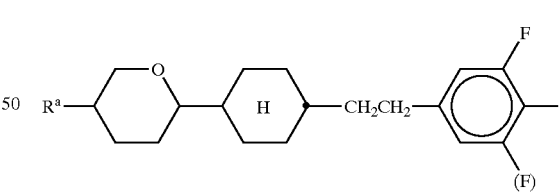

A-14
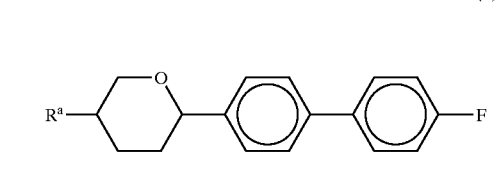

A-15 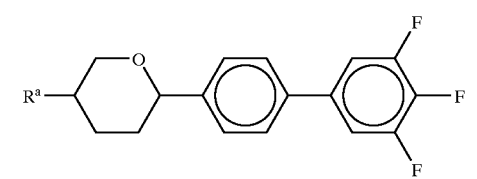
A-16 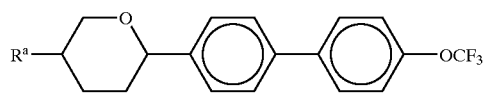
A-17 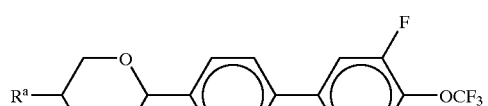
A-18 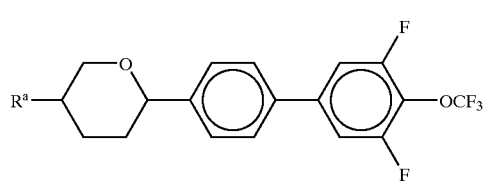
A-19 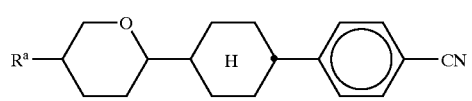
A-20 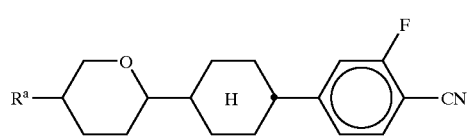
A-21 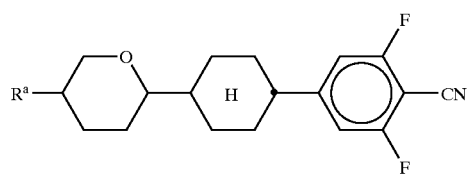
A-22 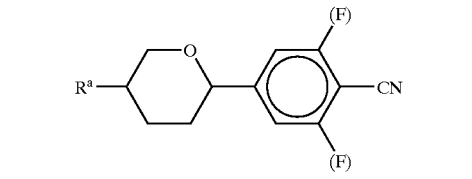
A-23 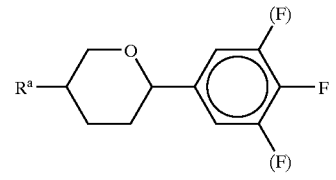
A-24 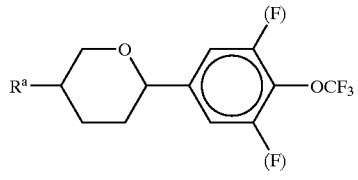
A-25 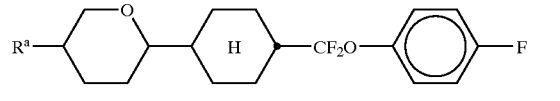
A-26 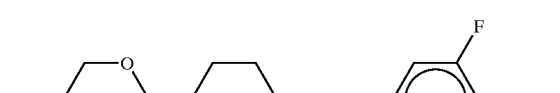
A-27 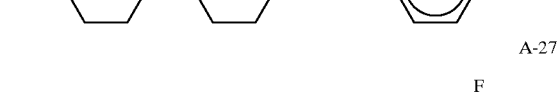
A-28 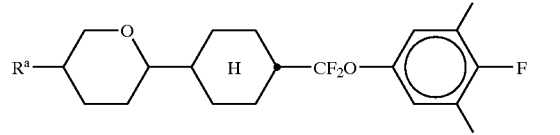
A-29 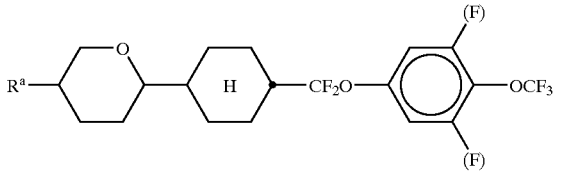
A-30 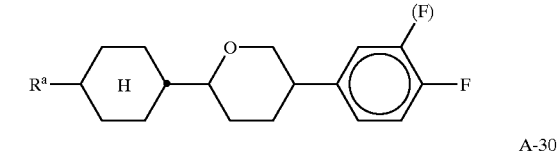
A-31 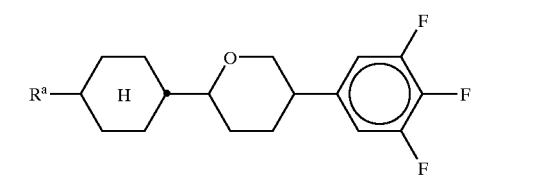
A-32 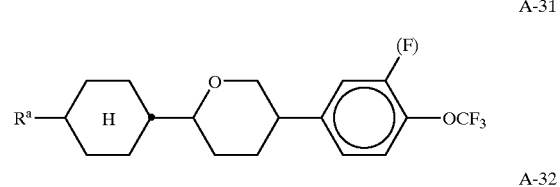
A-33 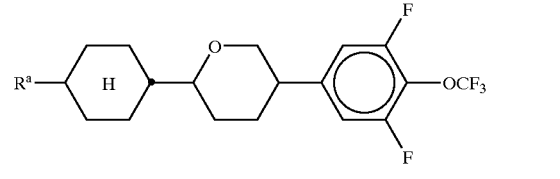
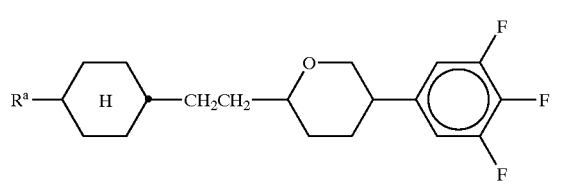

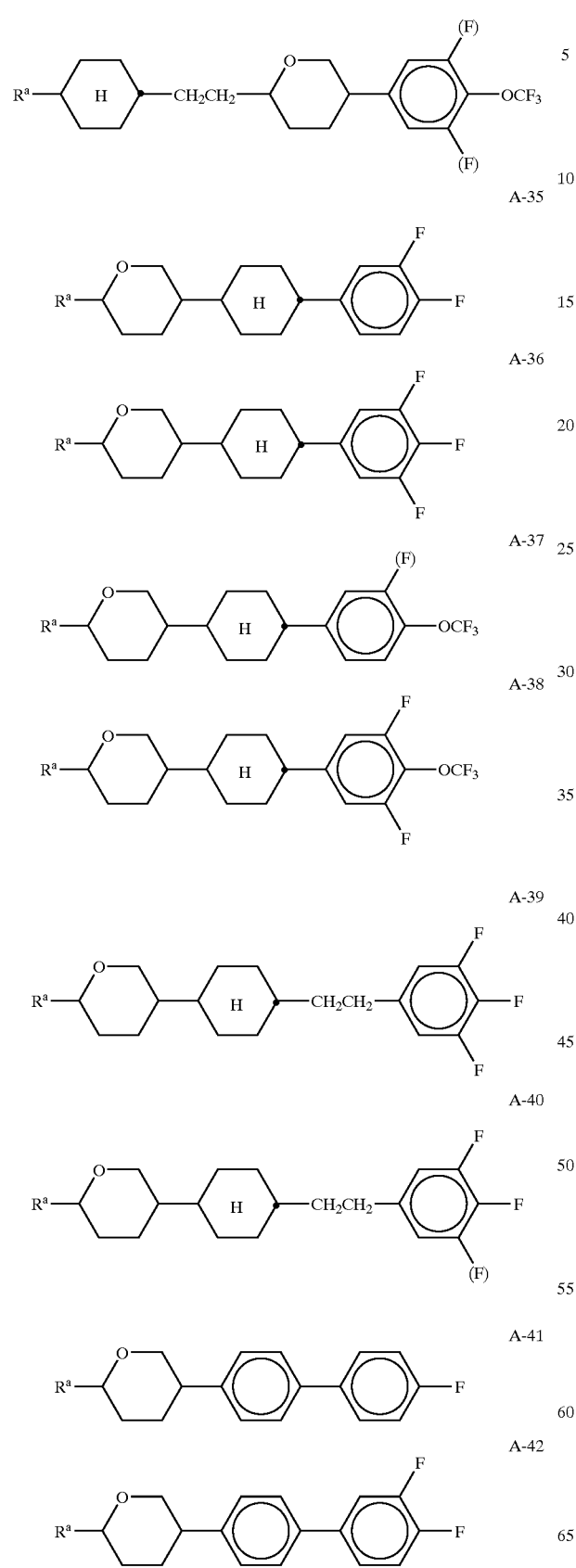

-continued
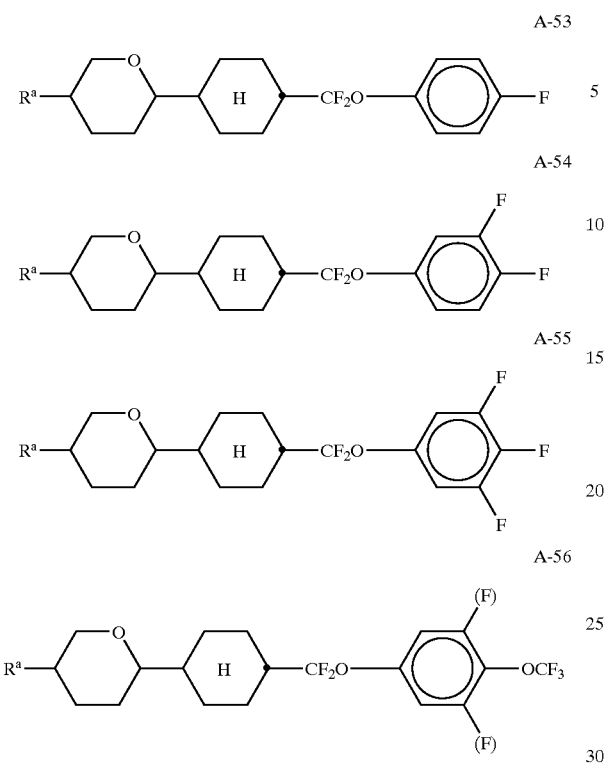
in which (F) is H or F.
3. A liquid-crystalline medium according to claim 1, wherein said medium contains at least one compound of formulae B-1 to B-6
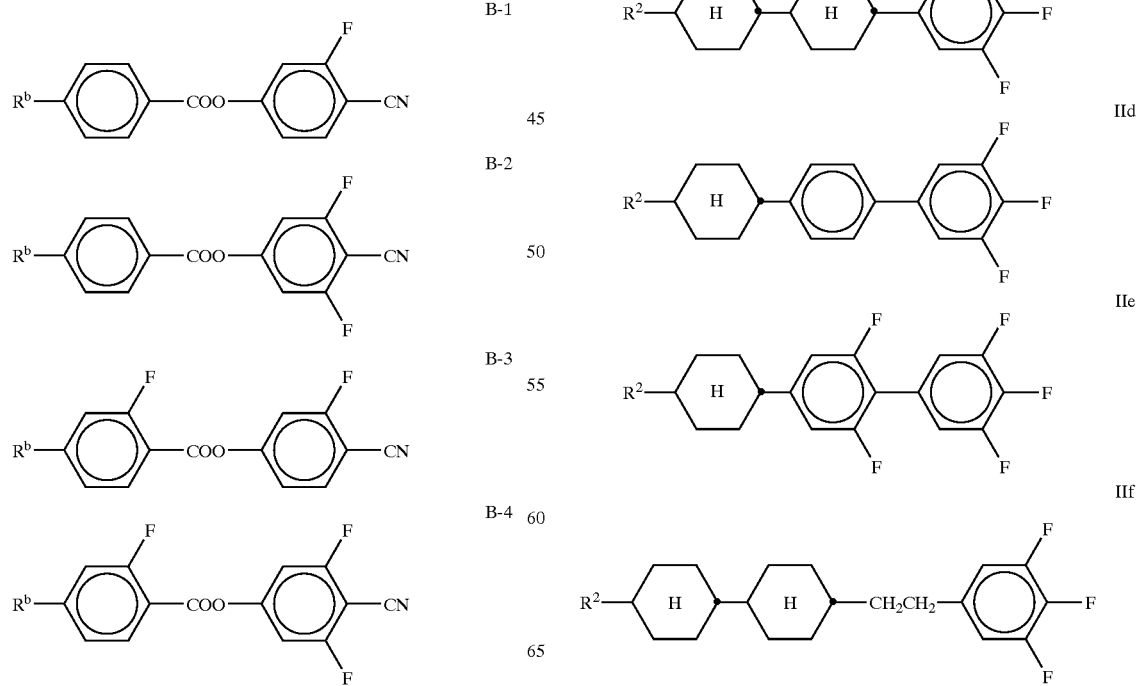
-continued
4. A liquid-crystal medium according to claim 1, further comprising at least one compound of formulae IIa to IIk
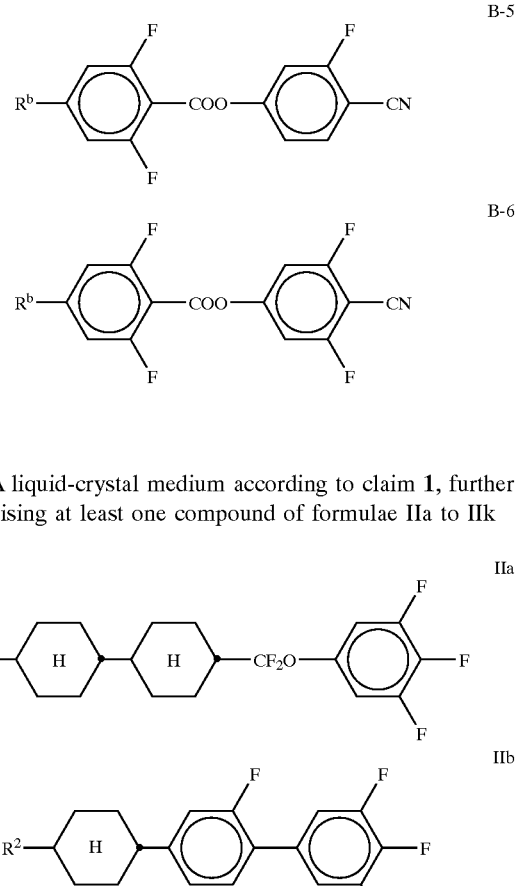

IIg
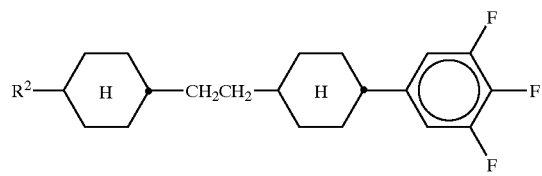

IIh
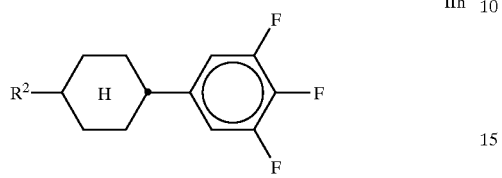

IIi
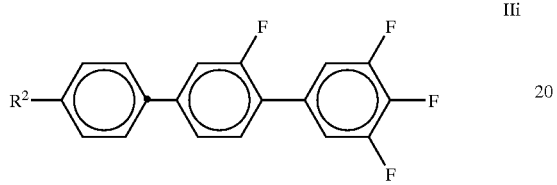

IIj
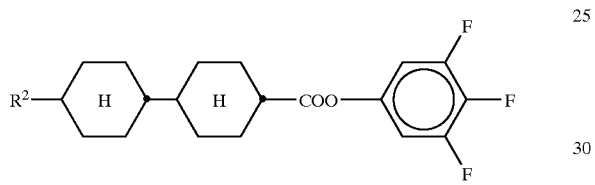

IIk
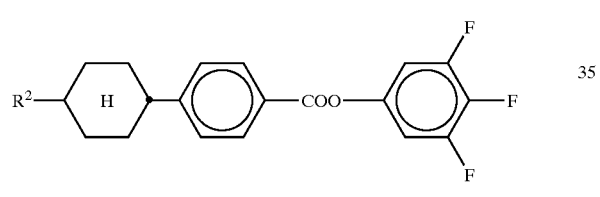

in which
R² is H, an alkyl radical having from 1 to 12 carbon atoms which is unsubstituted, monosubstituted by CN or CF₃ or at least monosubstituted by halogen, and in which one or more CH₂ groups are, independently of one another, optionally replaced by —O—, —S—,

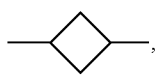

—CH=CH—, —C≡C—, —CO—, —CO—O—, —O—CO— or —O—CO—O— in such a way that O atoms are not linked directly to one another.

5. A liquid-crystal medium according to claim 1, further comprising one or more cyano compounds of formulae IIIa to IIIj IIIa
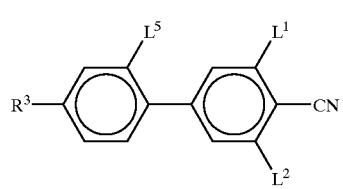

IIIb
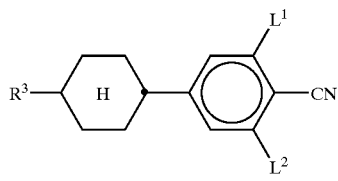

IIIc
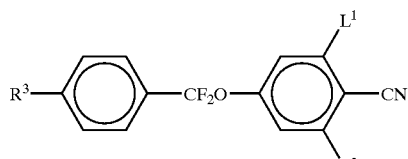

IIId
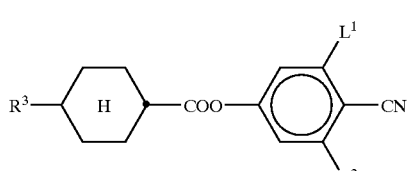

IIIe
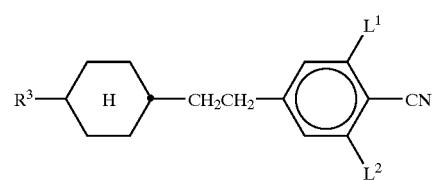

IIIf
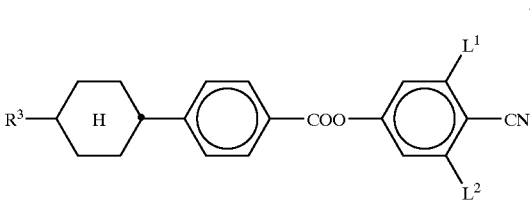

IIIg
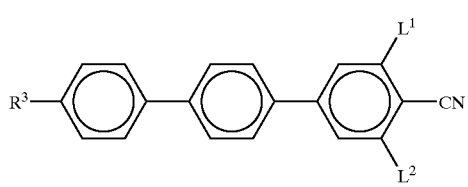

IIIh
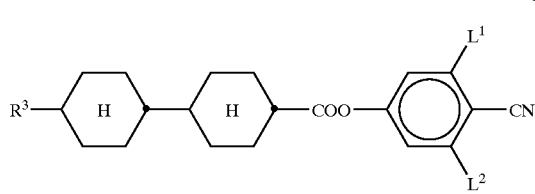

IIIi
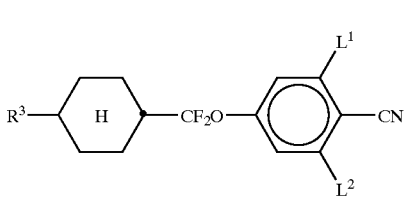

-continued

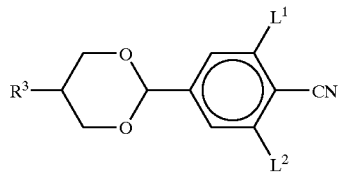
IIIj in which
R$^3$ is an alkyl radical having from 1 to 12 carbon atoms which is unsubstituted, monosubstituted by CN or CF$_3$ or at least monosubstituted by halogen, and in which one or more CH$_2$ groups are, independently of one another, optionally replaced by —O—, —S—,

—CH=CH—, —C≡C—, —CO—, —CO—O—, —O—CO— or —O—CO—O— in such a way that O atoms are not linked directly to one another, and L$^1$, L$^2$ and L$^5$ are each, independently of one another, H or F.

6. A liquid-crystal medium according to claim 1, further comprising one or more compounds of formula IV

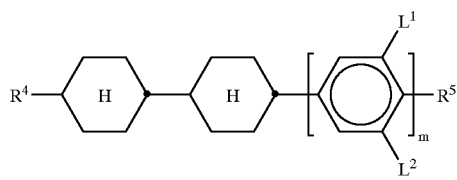
IV in which
m is 0 is 1,
R$^4$ is an alkenyl group having from 2 to 7 carbon atoms,
R$^5$ is H or an alkyl radical having from 1 to 12 carbon atoms which is unsubstituted, monosubstituted by CN or CF$_3$ or at least monosubstituted by halogen, and in which one or more CH$_2$ groups are each, independently of one another, optionally replaced by —O—, —S—,

—CH=CH—, —C≡C—, —CO—, —CO—O—, —O—CO— or —O—CO—O— in such a way that O atoms axe not linked directly to one another, or, if m is 1, R$^5$ can also be F, Cl, CF$_3$ or OCF$_3$, and L$^1$ and L$^2$ are each, independently of one another, H or F.

7. A liquid-crystalline medium according to claim 1, further comprising one or more compounds of formula VII

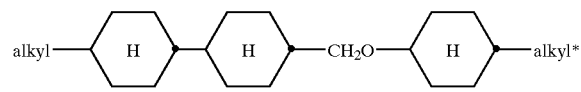
VII in which
alkyl and alkyl* are each, independently of one another, an alkyl group having from 1 to 7 carbon atoms.

8. A liquid-crystalline medium according to claim 1, further comprising one or more tolan compounds selected from formulae T2a, T2b and T2c

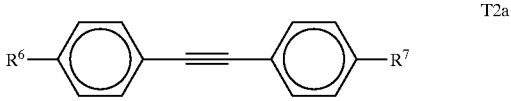
T2a

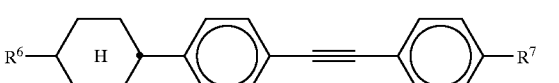
T2b

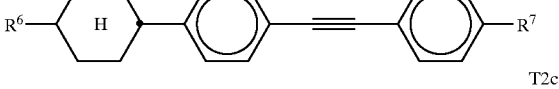
T2c

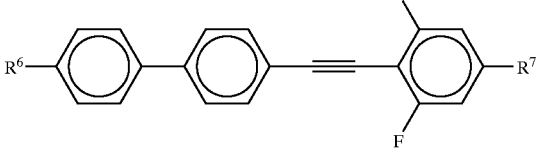

in which
R$^6$ and R$^7$ are an alkyl radical having from 1 to 12 carbon atoms which is unsubstituted, monosubstituted by CN or CF$_3$ or at least monosubstituted by halogen, and in which one or more CH$_2$ groups are, independently of one another, optionally replaced by —O—, —S—,

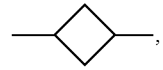

—CH=CH—, —C≡C—, —CO—, —CO—O—, —O—CO— or —O—CO—O— in such a way that O atoms are not linked directly to one another.

9. A liquid-crystalline medium according to claim 1, wherein said medium contains 5–30% by weight of compounds of the formula A.

10. A liquid-crystalline medium according to claim 1, wherein said medium contains 3–30% by weight of compounds of the formula B.

11. A liquid-crystalline medium according to claim 1, wherein said medium contains more than 20% of compounds having a dielectric anisotropy of Δ∈≧+12.

12. A liquid-crystalline medium according to 10, wherein said medium contains more than 20% of compounds having a dielectric anisotropy of Δ∈≧+12.

13. A method of generating an electrooptical effect comprising activating an electrooptical device containing a liquid-crystalline medium according to claim 1.

14. A method according to claim 13, wherein said device is a TN, STN or IPS device.

15. An electro-optical liquid-crystal display containing a liquid-crystalline medium according to claim 1.

16. A liquid-crystalline compound of formula A

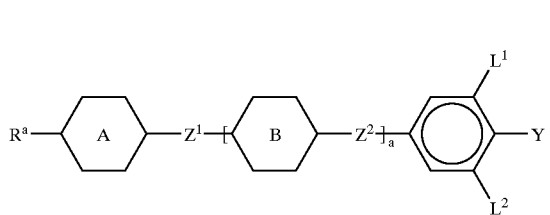

in which
R$^a$ is H or an alkyl radical having from 1 to 12 carbon atoms which is unsubstituted, monosubstituted by CN or CF$_3$ or at least monosubstituted by halogen, and in which one or more CH$_2$ groups are each, independently of one another, optionally replaced by —O—, —S—,

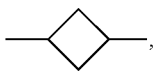

—CH=CH—, —C≡C—, —CO—, —CO—O—, —O—CO— or —O—CO—O— in such a way that O atoms are not linked directly to one another,

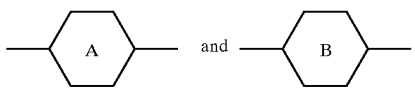

are each, independently of one another,

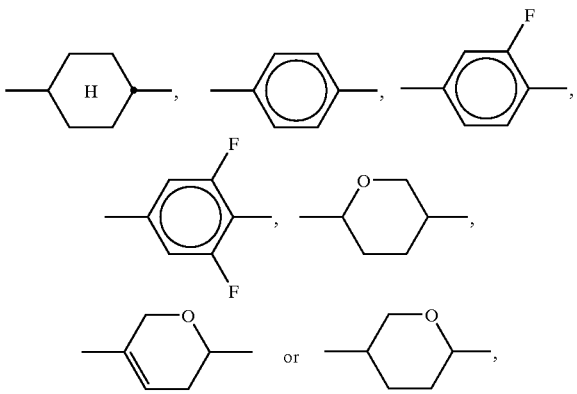

and
at least one ring is

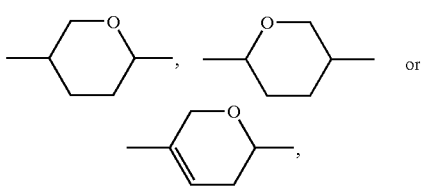

a is 0 is 1,
L$^1$ and L$^2$ are each, independently of one another, H or F,
Y is F, Cl, SF$_5$, NCS, OCN, SCN, or a monohalogenated or polyhalogenated alkyl, alkoxy, alkenyl or alkenyloxy radical, in each case having from 1 to 5 carbon atoms, and
Z$^1$ and Z$^2$ are each, independently of one another, —CH$_2$CH$_2$—, —(CH$_2$)$_4$—, —CH$^2$O—, —OCH$_2$—, —OCF$_2$—, —C≡C—, —CF=CF—, —CH=CH—, —COO—, —CH$_2$—, —(CH$_2$)$_3$— or a single bond.

17. A liquid-crystalline compound according to claim 16, wherein said compound is selected from formulae A-1 to A-24 and formulae A-29 to A-52,

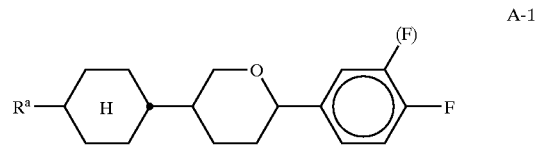
A-1

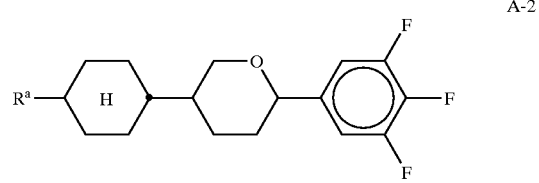
A-2

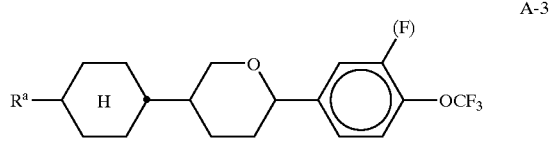
A-3

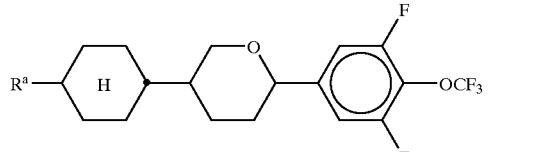
A-4

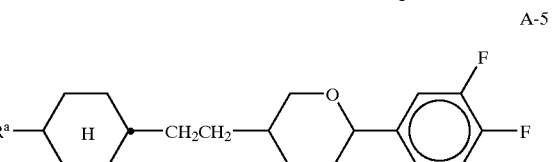
A-5

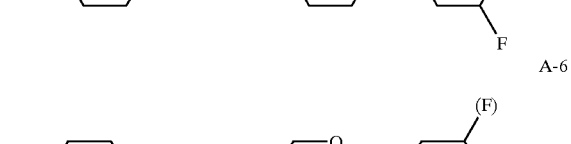
A-6

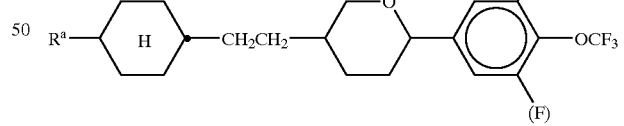
A-7

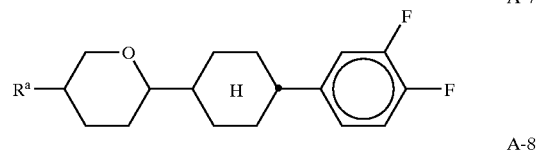
A-8

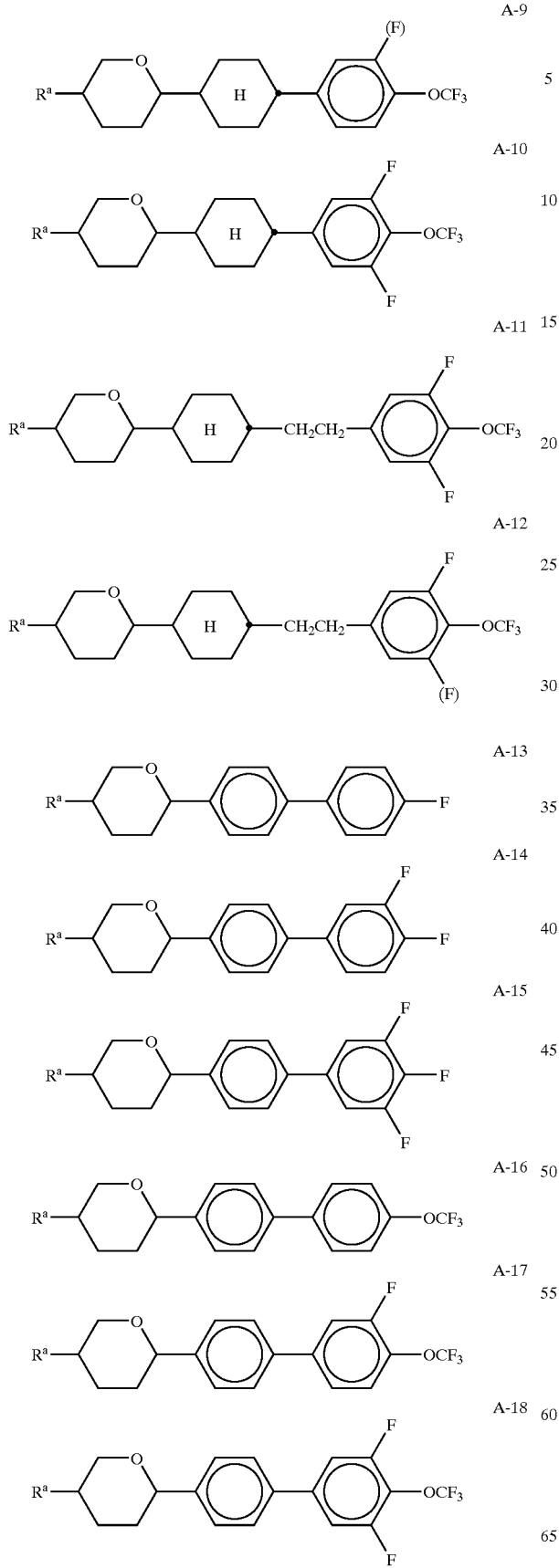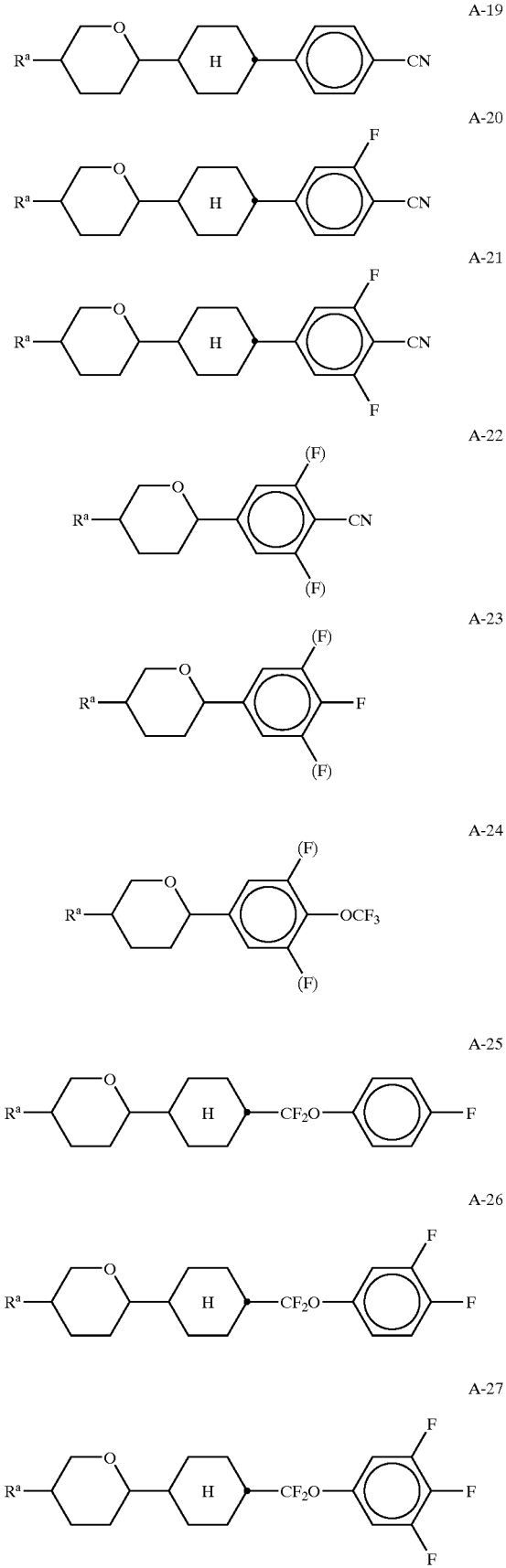

A-28
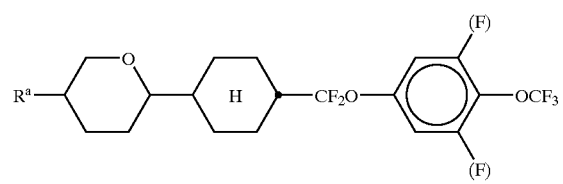
A-29
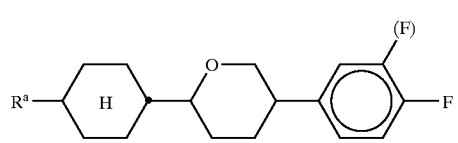
A-30
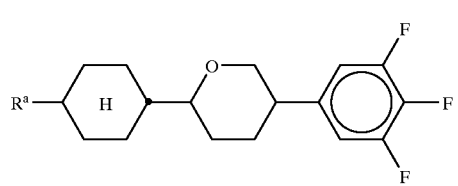
A-31
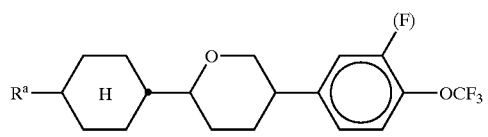
A-32
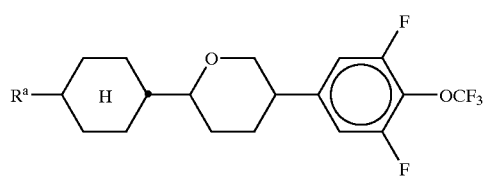
A-33
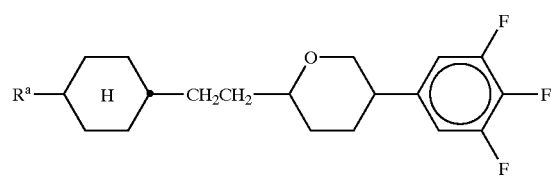
A-34
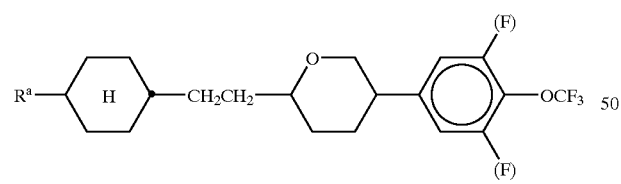
A-35
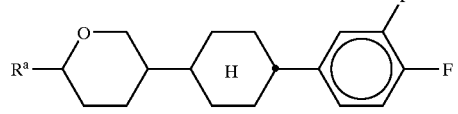
A-36
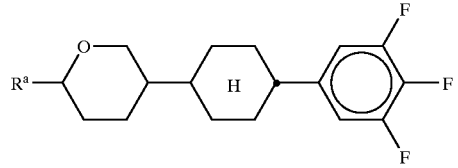
A-37
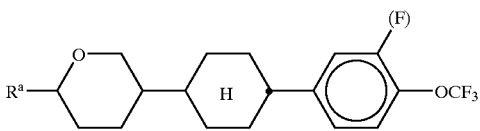
A-38
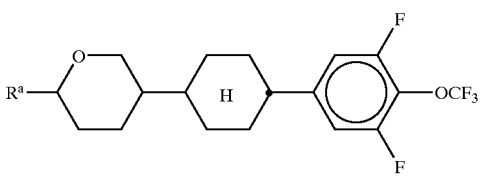
A-39
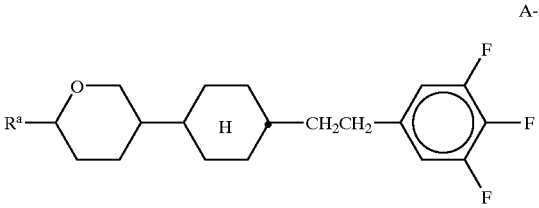
A-40
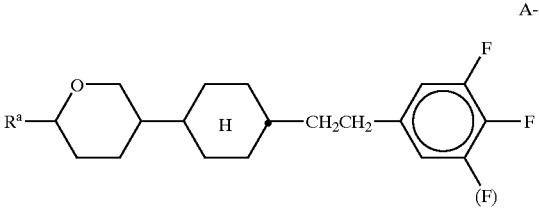
A-41
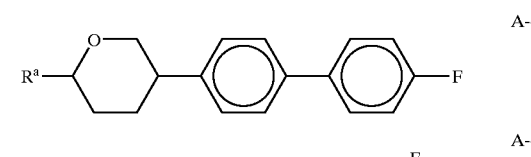
A-42
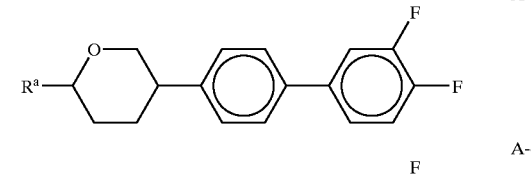
A-43
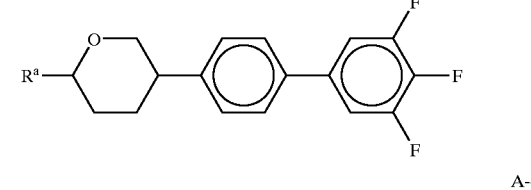
A-44
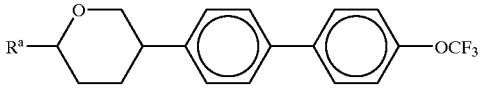
A-45
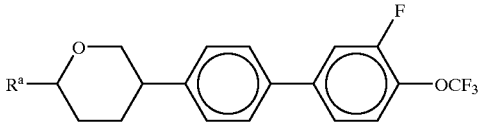
A-46
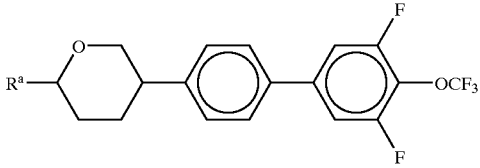

A-47 

A-48 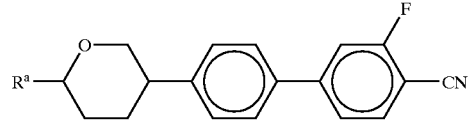

A-56 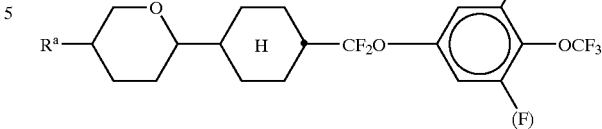

A-49 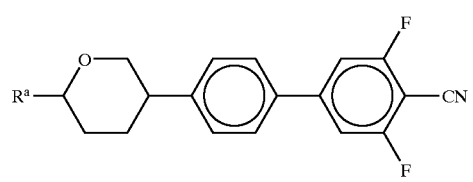

A-50 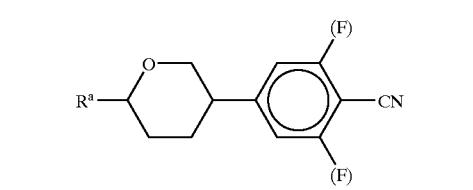

A-51 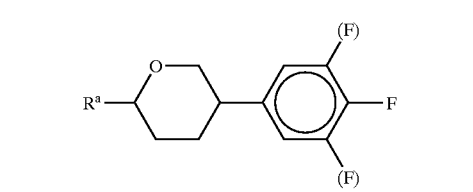

A-52 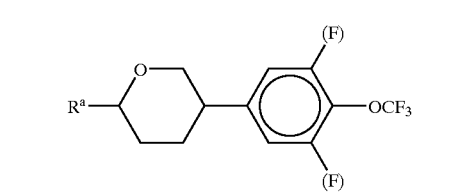

wherein (F) is H or F.

18. A TN or STN liquid-crystal display comprising two outer plates, which, together with a frame, form a cell, a nematic liquid-crystal mixture of positive dielectric anisotropy located in said cell, electrode layers with alignment layers on the insides of said outer plates, a tilt angle between the longitudinal axis of the molecules at the surface of the outer plates and the outer plates of 0–30 degrees, and a twist angle of said liquid-crystal mixture in the cell from alignment layer to alignment layer with a value of 22.5°–600°, wherein said a nematic liquid-crystal mixture comprises
a) 15–75% by weight of a liquid-crystalline component A consisting of one or more compounds having a dielectric anisotropy of greater than +1.5;
b) 2–85% by weight of a liquid-crystalline component B consisting of one or more compounds having a dielectric anisotropy of between −1.5 and +1.5;
c) 0–20% by weight of a liquid-crystalline component D consisting of one or more compounds having a dielectric anisotropy of below −1.5, and
d) optionally, an optically active component C in an amount whereby the ratio between the layer thickness and the natural pitch of the chiral nematic liquid-crystal mixture is 0.2 to 1.3; and wherein component A comprises at least one compound of formula A A-53 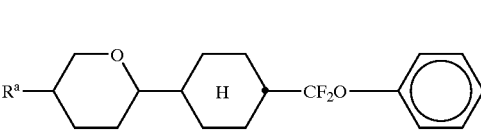

A-54 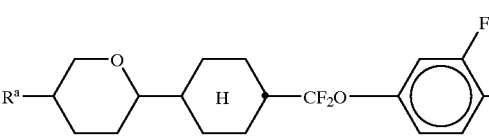

A-55 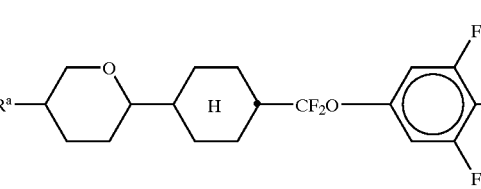

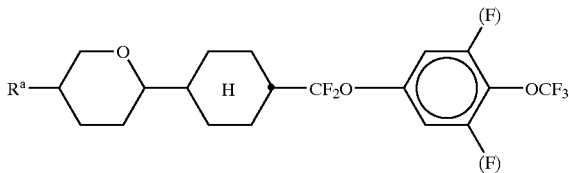

and at least one compound of formula B

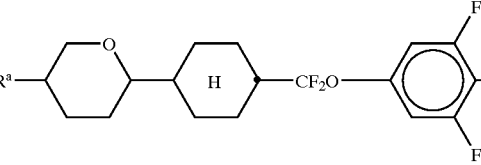

in which

R$^a$ and R$^b$ are each, independently of one another, H or an alkyl radical having from 1 to 12 carbon atoms which is unsubstituted, monosubstituted by CN or CF$_3$ or at least monosubstituted by halogen, and in which one or more CH$_2$ groups are, independently of one another, optionally replaced by —O—, —S—,

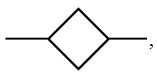

—CH=CH—, —C≡C—, —CO—, —CO—O—, —O—CO— or —O—CO—O— in such a way that O atoms are not linked directly to one another,

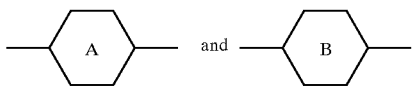

are each, independently of one another,

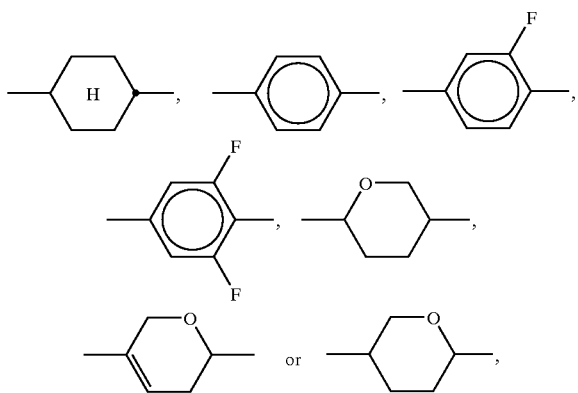

and
at least one ring is

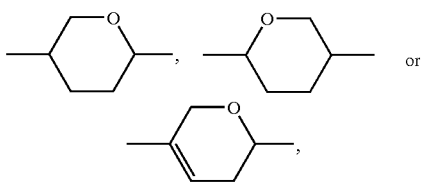

Z$^1$ and Z$^2$ are each, independently of one another, —CH$_2$CH$_2$—, —(CH$_2$)$_4$—, —CH$_2$O—, —OCH$_2$—, —CF$_2$O—, —OCF$_2$—, —C≡C—, —CF=CF—, —CH=CH—, —COO—, —CH$_2$—, —(CH$_2$)$_3$— or a single bond, a is 0 is 1, L$^1$ to L$^9$ are each, independently of one another, H or F, and Y is F, Cl, SF$_5$, NCS, OCN, SCN, or a monohalogenated or polyhalogenated alkyl, alkoxy, alkenyl or alkenyloxy radical, in each case having 1 to 5 carbon atoms.

19. A liquid-crystalline medium according to claim 2, wherein said medium contains at least one compound selected from formulae A-1, A-2, A-3, A-4, A-7, A-8, A-9, A-10, A-13, A-14, A-15, A-16, A-17, A-18, A-22, A-25, A-26, A-27, A-28, A-29, A-30, A-31, A-32, A-35, A-36, A-37, A-38, A-41, A-42, A-43, A-44, A-45, A-46, A-50, A-53, A-54, A-55 and A-56.

20. A liquid-crystalline medium according to claim 2, wherein said medium contains at least one compound selected from formulae A-2, A-8, A-15, A-17, A-18 and A-27.

21. A liquid-crystalline medium according to claim 2, wherein said medium contains at least one compound selected from formulae A-2 and A-8.

22. A liquid-crystalline compound according to claim 17, wherein said compound is selected from formulae A-1, A-2, A-3, A-4, A-7, A-8, A-9, A-10, A-13, A-14, A-15, A-16, A-17, A-18, A-22, A-29, A-30, A-31, A-32, A-35, A-36, A-37, A-38, A-41, A-42, A-43, A-44, A-45, A-46, A-50, A-53, A-54, A-55 and A-56.

23. A liquid-crystalline compound according to claim 17, wherein said compound is selected from formulae A-2, A-8, A-15, A-17, and A-18.

24. A liquid-crystalline compound according to claim 17, wherein said compound is selected from formulae A-2 and A-8.

25. A liquid-crystalline medium according to claim 3, wherein R$^b$ is a straight-chain alkyl radical having 1–7 carbon atoms or an alkenyl radical having 2–7 carbon atoms.

26. A liquid-crystalline medium according to claim 3, wherein said medium contains at least one compound of formulae B-1, B-2 or B-4.

27. A liquid-crystalline medium according to claim 1, wherein said medium further contains one or more compounds of formulae II*a to II*s II*a
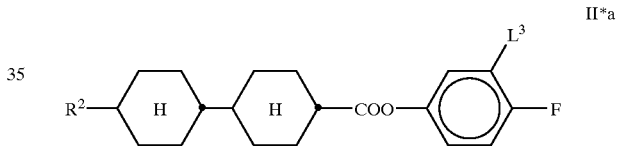

II*b
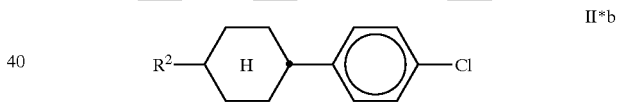

II*c
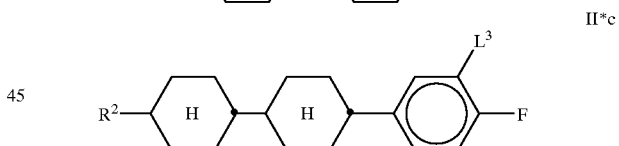

II*d
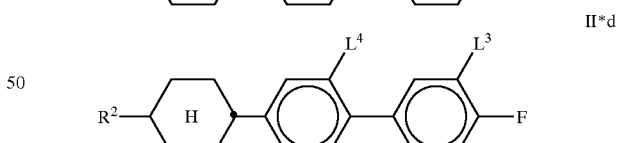

II*e
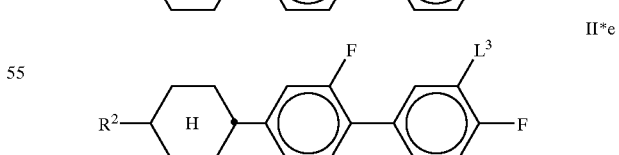

II*f
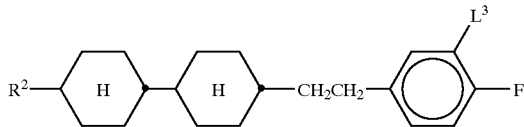

II*g 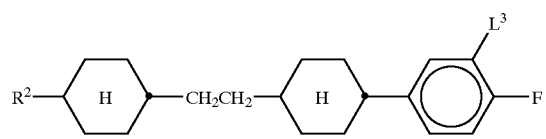

II*h 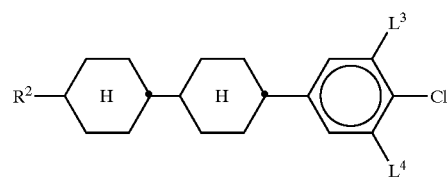

II*i 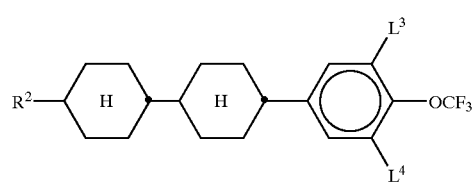

II*k 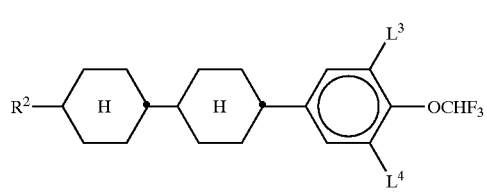

II*m 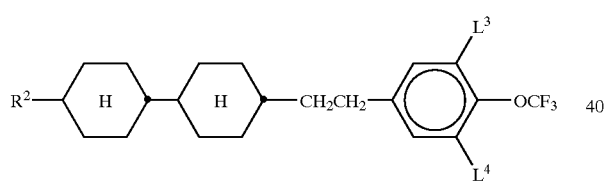

II*n 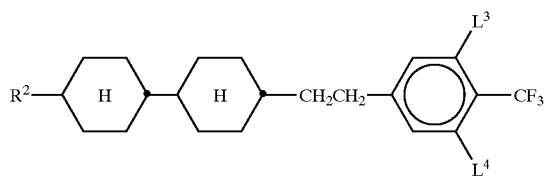

II*o 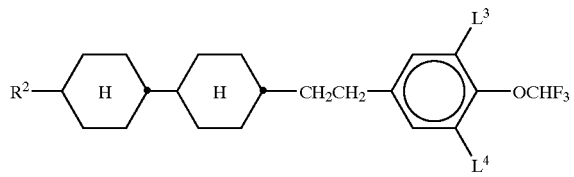

II*p 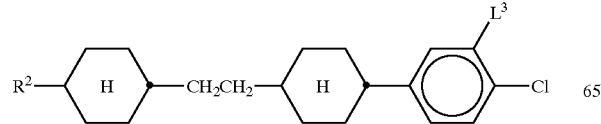

II*q 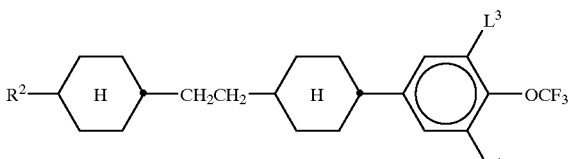

II*r 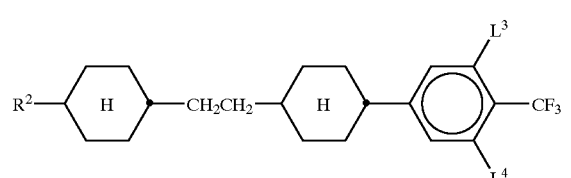

II*s 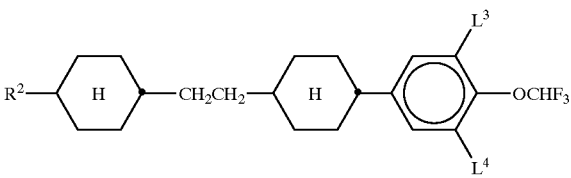

in which $R^2$ is H or an alkyl radical having from 1 to 12 carbon atoms which is un substituted, monosubstituted by CN or $CF_3$ or at least monosubstituted by halogen, and in which one or more $CH_2$ groups are each, independently of one another, optionally replaced by —O—, —S—,

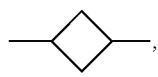

—CH=CH—, —C≡C—, —CO—, —CO—O—, —O—CO— or —O—CO—O— in such a way that O atoms are not linked directly to one another, and $L^3$ and $L^4$ are each, independently of one another, H or F.

28. A liquid-crystalline medium according to claim 5, wherein $R^3$ alkyl, alkenyl or alkoxy, in each case having up to 7 carbon atoms.

29. A liquid-crystalline medium according to claim 5, wherein said medium contains one or more compounds of the formulae IIIb, IIIc, IIIf and IIIj.

30. A liquid-crystalline medium according to claim 5, wherein said medium contains one or more compounds of the formulae IIIf and/or IIIg in which $L^2$ is H and $L^1$ is H or F.

31. A liquid-crystalline medium according to claim 1, wherein said medium additionally comprises one or more heterocyclic compounds of formula Va and/or formula Vb Va 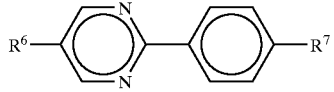

Vb 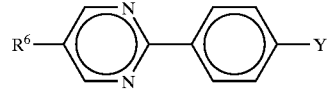

wherein

R⁶ and R⁷ are an alkyl radical having from 1 to 12 carbon atoms which is unsubstituted, monosubstituted by CN or CF₃ or at least monosubstituted by halogen, and in which one or more CH₂ groups are, independently of one another, optionally replaced by —O—, —S—,

—CH=CH—, —C≡C—, —CO—, —CO—O—, —O—CO— or —O—CO—O— in such a way that O atoms are not linked directly to one another, and Y is F or Cl, in which the proportion of the compounds from formulas Va and Vb is from 2 to 35%.

32. A liquid-crystalline medium according to claim 1, wherein said medium contains at least one compound of formula A-2

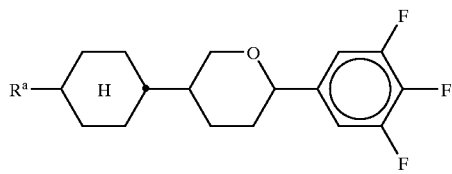

A-2 and at least one compound of formula B-1

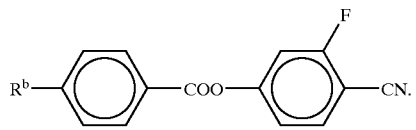

B-1

33. A liquid-crystalline medium according to claim 7, wherein said medium contains 2 to 30% by weight of compounds of the formula VII.

34. A liquid-crystalline medium according to claim 1, wherein said medium contains 5–30% by weight of compounds of formula A and 3–30% by weight of compounds of formula B.

35. A liquid-crystalline medium according to claim 1, wherein said medium contains 10–25% by weight of compounds of formula A and 3–20% by weight of compounds of formula B.

36. A liquid-crystalline medium according to claim 1, wherein said medium contains a total of three to six compounds of formulae A and B, and the proportion of compounds of formulae A and B with respect to the mixture as a whole is from 25to 65%.

37. A nematic liquid-crystal mixture comprising a) 15–75% by weight of a liquid-crystalline component A consisting of one or more compounds having a dielectric anisotropy of greater than +1.5;

b) 2–85% by weight of a liquid-crystalline component B consisting of one or more compounds having a dielectric anisotropy of between −1.5 and +1.5;

c) 0–20% by weight of a liquid-crystalline component D consisting of one or more compounds having a dielectric anisotropy of below −1.5, and d) optionally, an optically active component C in an amount whereby the ratio between the layer thickness and the natural pitch of the chiral nematic liquid-crystal mixture is 0.2 to 1.3; and wherein component A comprises at least one compound of formula A

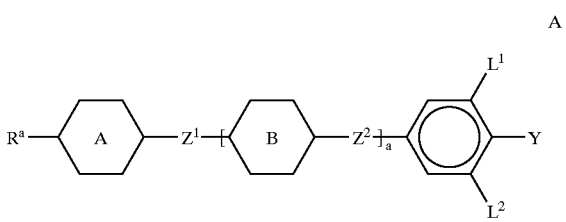

A and at least one compound of formula B

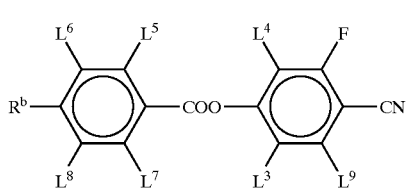

B in which

Rᵃ and Rᵇ are each, independently of one another, H or an alkyl radical having from 1 to 12 carbon atoms which is unsubstituted, monosubstituted by CN or CF₃ or at least monosubstituted by halogen, and in which one or more CH₂ groups are, independently of one another, optionally replaced by —O—, —S—,

—CH=CH—, —C≡C—, —CO—, —CO—O—, —O—CO— or —O—CO—O— in such a way that O atoms are not linked directly to one another,

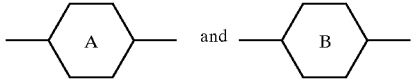

are each, independently of one another,

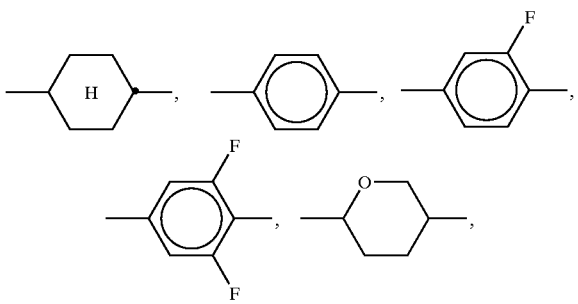

-continued

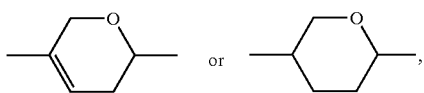

and at least one ring is

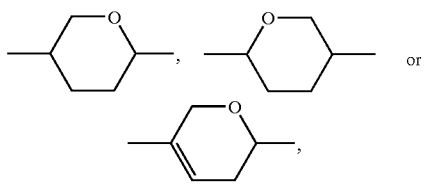

$Z^1$ and $Z^2$ are each, independently of one another, —CH$_2$CH$_2$—, —(CH$_2$)$_4$—, —CH$_2$O—, —OCH$_2$—, —CF$_2$O—, —OCF$_2$—, —C≡C—, —CF=CF—, —CH=CH—, —COO—, —CH$_2$—, —(CH$_2$)$_3$— or a single bond, a is 0 is 1, $L^1$ to $L^9$ are each, independently of one another, H or F, and Y is F, Cl, SF$_5$, NCS, OCN, SCN, or a monohalogenated or polyhalogenated alkyl, alkoxy, alkenyl or alkenyloxy radical, in each case having 1 to 5 carbon atoms.

38. A nematic liquid-crystal mixture according to claim 37, wherein said liquid-crystal mixture contains component A in a proportion of from 20% to 65%, and the compounds of component A have a dielectric anisotropy of $\Delta\epsilon \geq +3$.

39. A nematic liquid-crystal mixture according to claim 37, wherein said liquid-crystal mixture contains component B in a proportion of 5 to 80%.

* * * * *

UNITED STATES PATENT AND TRADEMARK OFFICE
CERTIFICATE OF CORRECTION

PATENT NO. : 6,902,777 B2  Page 1 of 3
APPLICATION NO. : 10/740601
DATED : June 7, 2005
INVENTOR(S) : Harald Hirschmann It is certified that error appears in the above-identified patent and that said Letters Patent is hereby corrected as shown below:

Column 54, line 31, reads "mono substituted" should read -- monosubstituted --
Column 54, line 41, reads "–O–CO–or" should read -- –O–CO– or --
Column 55, line 19, reads "to are each" should read -- are each --
Column 56, line 42, delete the formula and insert the following:

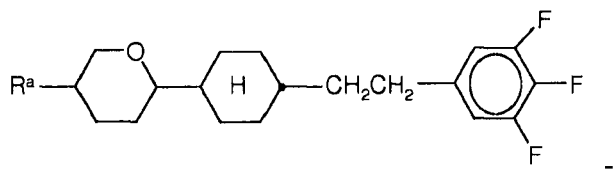

Column 59, line 52, delete the formula and insert the following:

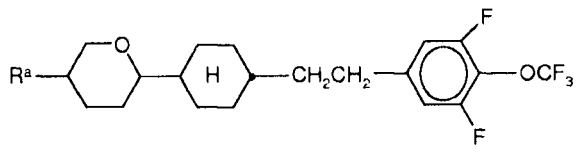

Column 60, line 29, delete the formula and insert the following:

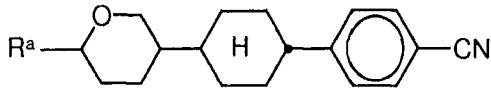

Column 60, line 35, delete the formula and insert the following:

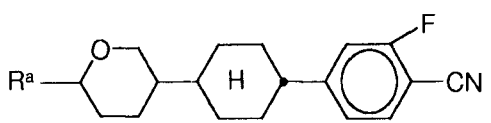

Column 60, line 41, delete the formula and insert the following:

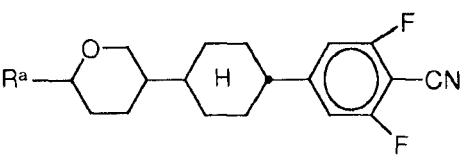

Column 61, line 5, delete the formula and insert the following:

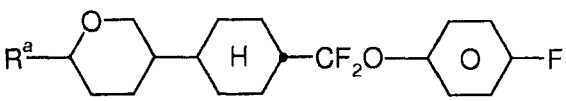

Column 61, line 12, delete the formula and insert the following:

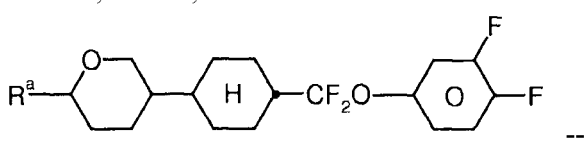

Column 61, line 18, delete the formula and insert the following:

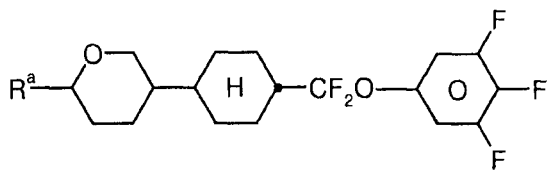

--                                                              --

Column 61, line 26, delete the formula and insert the following:

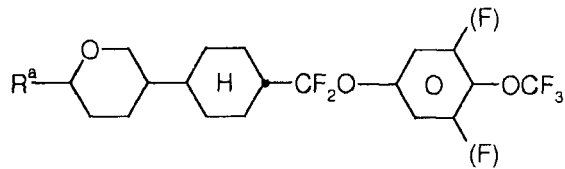

--                                                              --

Column 65, line 55, reads "atoms axe not" should read -- atoms are not --
Column 66, line 57, reads "to 10," should read -- to claim 10, --
Column 68, line 5, reads "-CH$^2$O-," should read -- -CH$_2$O-, --
Column 68, line 11, reads "to A-52" should read -- to A-56 --
Column 69, line 19, reads "-OCF$_3$" should read -- -F --
Column 70, lines 45-65, delete formulas A-25 through A-27
Column 71, lines 1-9, delete formula A-28
Column 72, line 27, reads "-F" should read -- -OCF$_3$ --
Column 73, line 5, delete the formula and insert the following:

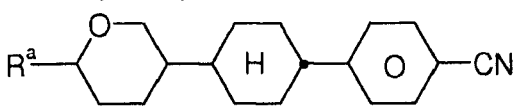

--                                                              --

Column 73, line 12, delete the formula and insert the following:

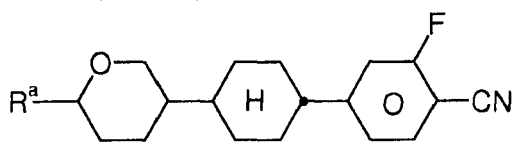

--                                                              --

Column 73, line 19, delete the formula and insert the following:

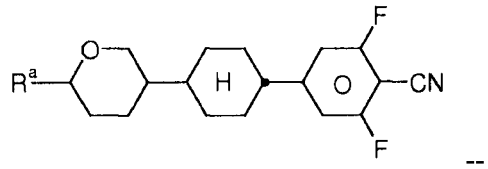

--                                                              --

Column 73, line 50, delete the formula and insert the follow

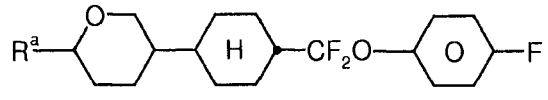

--                                                              --

CERTIFICATE OF CORRECTION (continued)
U.S. Pat. No. 6,902,777 B2

Column 73, line 57, delete the formula and insert the following:

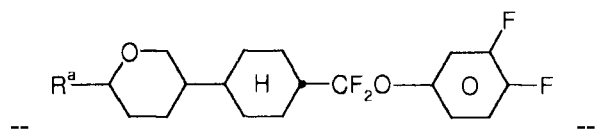

Column 73, line 63, delete the formula and insert the following:

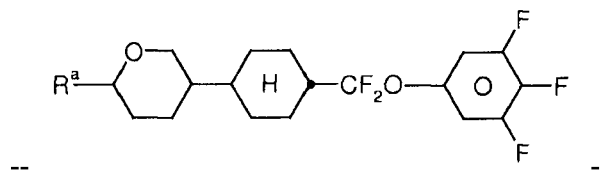

Column 74, line 29, reads "said a nematic" should read -- said nematic --
Column 75, line 53, reads "-OCF$_2$," should read -- -OCF$_2$-, --
Column 75, line 55, reads "0 is 1," should read -- 0 or 1, --
Column 77, line 32, reads "-OCHF$_3$" should read -- -OCHF$_2$ --
Column 78, line 23, reads "-OCHF$_3$" should read -- -OCHF$_2$ --
Column 78, line 30, reads "un substituted" should read -- unsubstituted --
Column 78, line 44, reads "R$^3$ alkyl", should read -- R$^3$ is alkyl --
Column 79, line 57, reads "25to" should read -- 25 to --

Signed and Sealed this

Thirteenth Day of April, 2010

David J. Kappos
*Director of the United States Patent and Trademark Office*